US006548503B1

(12) United States Patent
Adams et al.

(10) Patent No.: US 6,548,503 B1
(45) Date of Patent: Apr. 15, 2003

(54) PYRIDIN-4-YL OR PYRIMIDIN-4-YL SUBSTITUTED PYRAZINES

(75) Inventors: Jerry L. Adams, Wayne, PA (US); Ralph F. Hall, Villanova, PA (US); Jeffrey C. Boehm, King of Prussia, PA (US)

(73) Assignee: Smithkline Beecham Corporation, Philadelphia, PA (US)

( * ) Notice: Subject to any disclaimer, the term of this patent is extended or adjusted under 35 U.S.C. 154(b) by 0 days.

(21) Appl. No.: 09/806,858

(22) PCT Filed: Nov. 4, 1999

(86) PCT No.: PCT/US99/26119
§ 371 (c)(1),
(2), (4) Date: Apr. 5, 2001

(87) PCT Pub. No.: WO00/25791
PCT Pub. Date: May 11, 2000

Related U.S. Application Data

(60) Provisional application No. 60/107,013, filed on Nov. 4, 1998.

(51) Int. Cl.$^7$ ................... A61K 31/4965; C07D 403/00; C07D 241/02
(52) U.S. Cl. ................ 514/252.1; 514/255.05; 544/295; 544/296; 544/357
(58) Field of Search .............. 514/252.1, 255.05; 544/295, 357, 296

(56) References Cited

U.S. PATENT DOCUMENTS

| | | | |
|---|---|---|---|
| 2,833,779 A | 5/1958 | Fields .................. 260/296 |
| 3,707,475 A | 12/1972 | Lombardino ............. 260/309 |
| 3,772,441 A | 11/1973 | Lombardino ............. 424/273 |
| 3,929,807 A | 12/1975 | Fitzi ................ 260/294.8 R |
| 3,940,486 A | 2/1976 | Fitzi .................. 424/263 |
| 4,058,614 A | 11/1977 | Baldwin ............... 424/263 |
| 4,199,592 A | 4/1980 | Cherkofsky ............. 424/273 |
| 4,447,431 A | 5/1984 | Sallmann ............... 424/246 |
| 4,503,065 A | 3/1985 | Wilkerson .............. 514/396 |
| 4,565,875 A | 1/1986 | Cavender ............... 548/336 |
| 4,686,231 A | 8/1987 | Bender et al. .......... 514/333 |
| 4,822,805 A | 4/1989 | Tasasugi et al. ........ 514/341 |
| 4,886,807 A | 12/1989 | Kitamura et al. ........ 514/258 |
| 5,545,669 A | 8/1996 | Adams et al. .......... 514/562 |
| 5,559,137 A | 9/1996 | Adams et al. .......... 514/341 |
| 5,593,991 A | 1/1997 | Adams et al. ........ 514/235.2 |
| 5,593,992 A | 1/1997 | Adams et al. ........ 514/235.8 |
| 5,656,644 A | 8/1997 | Adams et al. .......... 514/341 |
| 5,658,903 A | 8/1997 | Adams et al. ........ 514/235.8 |
| 5,663,334 A | 9/1997 | Adams et al. .......... 544/122 |
| 5,670,527 A | 9/1997 | Adams et al. .......... 514/341 |
| 5,686,455 A | 11/1997 | Adams et al. .......... 514/256 |
| 5,716,955 A | 2/1998 | Adams et al. ........ 514/235.8 |
| 5,716,972 A | 2/1998 | Adams et al. .......... 514/314 |
| 5,739,143 A | 4/1998 | Adams et al. .......... 514/275 |
| 5,756,499 A | 5/1998 | Adams et al. ........ 514/235.8 |
| 5,777,097 A | 7/1998 | Lee et al. ............ 536/24.31 |
| 5,783,664 A | 7/1998 | Lee et al. ............. 530/350 |
| 5,811,549 A | 9/1998 | Adams et al. .......... 544/123 |
| 5,864,036 A | 1/1999 | Adams et al. .......... 544/123 |
| 5,869,043 A | 2/1999 | McDonnell et al. ...... 424/94.1 |
| 5,869,660 A | 2/1999 | Adams et al. .......... 544/122 |
| 5,871,934 A | 2/1999 | Lee et al. ............. 435/7.1 |
| 5,916,891 A | 6/1999 | Adams et al. .......... 514/256 |
| 5,917,043 A | 6/1999 | Sisko .................. 544/332 |
| 5,929,076 A | 7/1999 | Adams et al. .......... 514/252 |
| 5,955,366 A | 9/1999 | Lee et al. ............. 435/471 |
| 5,969,184 A | 10/1999 | Adams et al. ........... 564/154 |
| 5,977,103 A | 11/1999 | Adams et al. ......... 514/235.2 |
| 5,998,425 A | 12/1999 | Adams et al. .......... 514/275 |
| 6,008,235 A | 12/1999 | Adams et al. .......... 514/333 |
| 6,096,739 A | 8/2000 | Feurstein ............ 514/235.2 |
| 6,150,373 A | 11/2000 | Harris et al. .......... 514/258 |
| 6,235,760 B1 | 5/2001 | Feurstein ............. 514/341 |
| 6,288,062 B1 | 9/2001 | Adams et al. ......... 514/236.8 |
| 6,335,340 B1 | 1/2002 | Gallagher et al. ..... 514/252.05 |
| 6,362,193 B1 | 3/2002 | Adams .................. 514/274 |

FOREIGN PATENT DOCUMENTS

| | | | |
|---|---|---|---|
| EP | 0 431 421 A2 | 11/1990 | |
| EP | 431421 | * 6/1991 | |
| EP | 0 477 049 A1 | 3/1992 | ......... C07D/231/14 |
| EP | 0 477 049 B1 | 12/1999 | ......... C07D/231/14 |
| WO | WO 91/19497 | 12/1991 | .......... A61K/31/44 |
| WO | WO 92/10190 | 6/1992 | .......... A61K/31/44 |
| WO | WO 92/10498 | 6/1992 | .......... C07D/487/00 |
| WO | WO 92/12154 | 7/1992 | .......... C07D/487/04 |
| WO | WO 93/14081 | 7/1993 | .......... C07D/401/04 |
| WO | WO 93/14082 | 7/1993 | .......... C07D/401/04 |
| WO | WO 94/19350 | 9/1994 | .......... C07D/487/04 |
| WO | WO 95/02591 | 1/1995 | .......... C07D/401/04 |
| WO | WO 95/03297 | 2/1995 | .......... C07D/401/04 |
| WO | WO 95/09847 | 4/1995 | |
| WO | WO 95/09851 | 4/1995 | |
| WO | WO 95/09852 | 4/1995 | |
| WO | WO 95/09853 | 4/1995 | |
| WO | WO 95/13067 | 5/1995 | .......... A61K/31/44 |
| WO | WO 95/31451 | 11/1995 | .......... C07D/401/04 |
| WO | WO 95/33461 | 12/1995 | .......... A61K/31/195 |
| WO | WO 96/21452 | 7/1996 | .......... A61K/31/535 |

(List continued on next page.)

OTHER PUBLICATIONS

Lucia et al., "Photoinduced Charge Separation Promoted by Ring Opening of a Piperazine Radical Cation", J.Am. Chem. Soc., 1996, 118, pp. 3057–3058.
Armarego, W.J. Chem. Soc., (JCSOA9) p. 561 (1962).
Badger et al., "Protective Effect of SK&F 86002, a Novel Dual Inhibitor of Arachidonic Acid . . . ", Circulatory Shock, vol. 27, 1991, pp. 51–61.

(List continued on next page.)

Primary Examiner—Richard L. Raymond
Assistant Examiner—Sudhaker B. Patel
(74) Attorney, Agent, or Firm—Dara L. Dinner; Stephen Venetianer; Charles M. Kinzig

(57) ABSTRACT

The present invention is directed to novel pyridin-4-yl or pyrimidin-4-yl substituted pyrazine compounds and compositions for use in therapy.

23 Claims, No Drawings

FOREIGN PATENT DOCUMENTS

| | | | |
|---|---|---|---|
| WO | WO 96/21654 | 7/1996 | ......... C07D/233/00 |
| WO | WO 96/40143 | 12/1996 | ......... A61K/31/505 |
| WO | WO 97/05877 | 2/1997 | ......... A61K/31/44 |
| WO | WO 97/05878 | 2/1997 | ......... A61K/31/44 |
| WO | WO 97/12876 | 4/1997 | ......... C07D/233/76 |
| WO | WO 97/16426 | 5/1997 | ......... C07D/207/30 |
| WO | WO 97/16441 | 5/1997 | ......... C07D/401/04 |
| WO | WO 97/16442 | 5/1997 | ......... C07D/401/04 |
| WO | WO 97/23479 | 7/1997 | ......... C07D/401/14 |
| WO | WO 97/25045 | 7/1997 | ......... A61K/31/505 |
| WO | WO 97/25046 | 7/1997 | ......... A61K/31/505 |
| WO | WO 97/25047 | 7/1997 | ......... A61K/31/505 |
| WO | WO 97/25048 | 7/1997 | ......... A61K/31/505 |
| WO | WO 97/32583 | 9/1997 | ......... A61K/31/44 |
| WO | WO 97/33883 | 9/1997 | |
| WO | WO 97/35855 | 10/1997 | ......... C07D/401/04 |
| WO | WO 97/35856 | 10/1997 | ......... C07D/401/04 |
| WO | WO 97/36587 | 10/1997 | ......... A61K/31/44 |
| WO | WO 97/47618 | 12/1997 | ......... C07D/403/14 |
| WO | WO 98/03484 | 1/1998 | ......... C07D/213/34 |
| WO | WO 98/06715 | 2/1998 | ......... C07D/403/06 |
| WO | WO 98/07425 | 2/1998 | ......... A61K/31/44 |
| WO | WO 98/16230 | 4/1998 | ......... A61K/31/535 |
| WO | WO 98/22109 | 5/1998 | ......... A61K/31/44 |
| WO | WO 98/22457 | 5/1998 | ......... C07D/401/04 |
| WO | WO 98/24780 | 6/1998 | |
| WO | WO 98/24782 | 6/1998 | |
| WO | WO 98/25619 | 6/1998 | ......... A61K/31/505 |
| WO | WO 98/27098 | 6/1998 | ......... C07D/487/04 |
| WO | WO 98/28292 | 7/1998 | ......... C07D/401/00 |
| WO | WO 98/47892 | 10/1998 | ......... C07D/401/04 |
| WO | WO 98/48799 | 11/1998 | ......... C07D/471/04 |
| WO | WO 98/52558 | 11/1998 | ......... A61K/31/34 |
| WO | WO 98/52937 | 11/1998 | ......... C07D/401/00 |
| WO | WO 98/52940 | 11/1998 | ......... C07D/401/04 |
| WO | WO 98/52941 | 11/1998 | ......... C07D/401/04 |
| WO | WO 98/56377 | 12/1998 | ......... A61K/31/44 |
| WO | WO 98/56788 | 12/1998 | ......... C07D/405/14 |
| WO | WO 98/57966 | 12/1998 | ......... C07D/403/02 |
| WO | WO 99/00357 | 1/1999 | ......... C07C/275/28 |
| WO | WO 99/01130 | 1/1999 | ......... A61K/31/44 |
| WO | WO 99/01131 | 1/1999 | ......... A61K/31/445 |
| WO | WO 99/01136 | 1/1999 | ......... A61K/31/53 |
| WO | WO 99/01449 | 1/1999 | ......... C07D/401/04 |
| WO | WO 99/01452 | 1/1999 | ......... C07D/403/04 |
| WO | WO 99/03837 | 1/1999 | ......... C07D/233/54 |
| WO | WO 99/17776 | 4/1999 | ......... A61K/31/505 |
| WO | WO 99/18942 | 4/1999 | ......... A61K/31/00 |
| WO | WO 99/32110 | 7/1999 | ......... A61K/31/415 |
| WO | WO 99/32121 | 7/1999 | ......... A61K/31/505 |
| WO | WO 99/42592 | 8/1999 | ......... C12N/15/54 |
| WO | WO 99/57101 | 11/1999 | ......... C07D/231/38 |
| WO | WO 99/57253 | 11/1999 | ......... C12N/9/00 |
| WO | WO 99/58128 | 11/1999 | ......... A61K/31/44 |
| WO | WO 99/58202 | 11/1999 | ......... C07D/213/56 |
| WO | WO 99/58523 | 11/1999 | ......... C07D/401/04 |
| WO | WO 99/59959 | 11/1999 | ......... C07C/235/56 |
| WO | WO 99/59960 | 11/1999 | ......... C07C/235/56 |
| WO | WO 99/61426 | 12/1999 | ......... C07D/235/06 |
| WO | WO 99/61437 | 12/1999 | ......... C07D/401/04 |
| WO | WO 99/61440 | 12/1999 | ......... C07D/403/14 |
| WO | WO 99/64400 | 12/1999 | ......... C07D/217/24 |
| WO | WO 00/01688 | 1/2000 | ......... C07D/401/04 |
| WO | WO 00/06563 | 2/2000 | ......... C07D/401/04 |
| WO | WO 00/07980 | 2/2000 | ......... C07C/237/42 |
| WO | WO 00/07991 | 2/2000 | ......... C07D/213/82 |
| WO | WO 00/10563 | 3/2000 | ......... A61K/31/34 |
| WO | WO 00/12074 | 3/2000 | ......... A61K/31/00 |
| WO | WO 00/12497 | 3/2000 | ......... C07D/401/00 |
| WO | WO 00/17175 | 3/2000 | ......... C07D/277/48 |
| WO | WO 00/18738 | 4/2000 | ......... C07D/213/82 |
| WO | WO 00/19824 | 4/2000 | ......... A01N/43/42 |
| WO | WO 00/20402 | 4/2000 | ......... C07D/239/94 |
| WO | WO 00/23072 | 4/2000 | ......... A61K/31/352 |
| WO | WO 00/25791 | 5/2000 | ......... A61K/31/496 |
| WO | WO 00/26209 | 5/2000 | ......... C07D/403/04 |
| WO | WO 00/31063 | 6/2000 | ......... C07D/401/04 |
| WO | WO 00/31065 | 6/2000 | ......... C07D/401/04 |
| WO | WO 00/31072 | 6/2000 | ......... C07D/409/06 |
| WO | WO 00/35911 | 6/2000 | ......... C07D/405/14 |
| WO | WO 00/39116 | 7/2000 | ......... C07D/401/04 |
| WO | WO 00/40243 | 7/2000 | ......... A61K/31/444 |
| WO | WO 00/41698 | 7/2000 | ......... A61K/31/535 |
| WO | WO 00/43384 | 7/2000 | ......... C07D/401/12 |
| WO | WO 00/59541 | 10/2000 | ......... A61K/45/00 |
| WO | WO 00/75131 | 12/2000 | ......... C07D/401/04 |
| WO | WO 01/00229 | 1/2001 | ......... A61K/38/19 |
| WO | WO 01/19322 | 3/2001 | |
| WO | WO 01/37837 | 5/2001 | ......... A61K/31/517 |
| WO | WO 01/38312 | 5/2001 | ......... C07D/239/80 |
| WO | WO 01/38313 | 5/2001 | ......... C07D/239/80 |
| WO | WO 02/07772 | 1/2002 | ......... A61K/47/48 |
| WO | WO 02/058695 | 8/2002 | ......... A61K/31/395 |
| WO | WO 02/059083 | 8/2002 | |
| WO | WO 02/060869 | 8/2002 | |

OTHER PUBLICATIONS

Becker et al., J. Immunol., 147, p. 4307 (1991).
Boehm et al., J. Med. Chem. 39, pp. 3929–3937 (1996).
Bradlerova et al., Chem Zvesti, 29 (6), pp. 795–802 (1975).
Colotta et al., J. Immunol., 132(2), p.936 (1984).
de Silva et al., J. Chem. Soc., 4, pp. 685–690, (1995).
Dinarello et al., Rev.Infect.Disease, 6, p. 51 (1984).
Dinarello, J.Clin.Immun., 5(5), p. 287–297 (1985).
Engel & Steglich, Liebigs Ann. Chem., 1916 (1978).
Ferles et al., Collect. Czech. Chem. Commun., 5 (46), pp 1167–1172 (1981).
Fischer et al., Rec.Trav.Chim.Pays.Bas., 84, p. 439 (1965).
Fulmer et al., J. Heterocycl. Chem., 17 (4), pp. 799–800 (1980).
Gallahger et al., Bioorganic & Medicinal Chem. vol. 5, No. 1, pp. 49–64 (1997).
Garigipati, R., Tetrahedron Letters, 31, p. 190 (1989).
Gilbert, Synthesis, pp. 30–32 (1972).
Griswold et al., "Differentiation in vivo of classical non–steroidal antiinflammatory drugs . . . ", Drugs Exptl. Clin. Res., XIX(6), 1993, pp. 243–248.
Griswold et al., "Effect of Inhibots of Eicosanoid Metabolism in Murine Collagen–Induced Arthritis", Arthritis and Rheumatism, vol. 31, No. 11, Nov. 1998, pp. 1406–1412.
Ishibashi, Chem. Pharm. Bull., 37(8), pp. 2214–2216 (1989).
Johnson, P.A., J.Chem.Soc., Perkin Trans., vol. 1, pp. 285–905 (1996).
Jurkowski–Kowalczyk, Rocz. Chem., 51 (6), pp. 1191–9 (1977).
Katritzky, Synthesis, pp. 45–47 (1993).
Kawasaki et al., J. Bio. Chem., 272(30), pp. 18518–18521.
Kumada et al., Tetrahedron Letters, 22, p. 5319 (1981).
Lamartina et al., Boll. Chim. Farm., 129 (12), pp. 314–316 (1990).
Lee et al., "Bicyclic Imidazoles as a Novel Class of Cytokine Biosynthesis Inhibitors", Annals NY Academy of Sciences, vol. 696, 1993, pp. 149–170.
Mikailu et al., Zh. Obshch. Khim., 56 (7), pp. 1513–1517 (1986) Not In English!.

Morton et al., Tetrahedron Letters, 4123 (1982).

Olivera et al., "Beneficial Effects of SK&F 105809, a Novel Cytokine–Suppressive Agent, in Murine Models of Endotoxin Shock", Circulatory Shock, 37, 1992, pp. 301–306.

Poli et al., Proc.Nat'l Acad.Sci., 87, p.782–784 (1990).

Pridgen, J.Org.Chem., 47, p. 4319 (1982).

Protecting Groups in Organic Synthesis, Second Edition, Greene TW and Wuts PGM, Wiley–Interscience, New York 1991, pp. 10–174 (hydroxyl and phenolic) and pp. 309–403 (NH protection).

R.P.Soni, Aust.J.Chem., 35, p. 1493–6 (1982).

Santilli et al., "Thieno[2,3–d]pyrimidines. I. A New Method for the Preparation of Esters . . . ", J. Heterocycl Chem., vol. 8, 1971, pp. 445–453.

Simon et al., J. Immunol. Methods, 84, p. 85 (1985).

Snieckus, V., Tetrahedron Letters, 29, 2135 (1988).

Stille, J.Amer.Chem.Soc., 109, p. 5478 (1978).

Strzybny et al., J. Org. Chem., 28, p. 3381 (1963).

Szucs et al., Chem. Zvesti, 26 (4), pp. 354–359 (1972).

Szucs et al., Acta fac. Pharm. Univ. Commenianae, 30, pp. 127–146 (1977) Not In English!.

Terashimia, M., Chem.Pharm.Bull., 11, p. 4755 (1985).

Thompson, W.J., et al., J.Org.Chem., 49, p. 5237 (1984).

Uno, Bull. Chem. Soc. Japan., vol. 69, pp. 1763–1767 (1996).

VanLeusen et al., J.O.C., 42, p. 1153 (1977).

Vartanyan et al., 40, (9), pp. 552–560 (1987) Not In English!.

Votta et al., "Inhibition of Human Monocyte IL–1 Production by SK&F 86002", Int. J. Immunotherapy, VI(1), 1990, pp. 1–12.

Warrior et al., "Development of a p38 Kinase Binding Assay for Hight Throughput Screening", Journal of Biomolecular Screening, vol. 4, No. 3, 1999, pp. 129–135.

Wilson et al., Chemistry & Biology, vol. 4, No. 6, pp 423–431 (1997).

Zavyalov, et al., Khim Farm Zh, 26(3), p. 88 (1992) (With Translation).

* cited by examiner

PYRIDIN-4-YL OR PYRIMIDIN-4-YL SUBSTITUTED PYRAZINES

This application is the §371 national stage entry of International Application PCT/US99/26119, filed Nov. 4, 1999, which claims benefit from Provisional Application U.S. Ser. No. 60/107,013, filed Nov. 4, 1998.

FIELD OF THE INVENTION

This invention relates to novel pyrazine substituted compounds, processes for the preparation thereof, the use thereof in treating cytokine mediated diseases and pharmaceutical compositions for use in such therapy.

BACKGROUND OF THE INVENTION

Intracellular signal transduction is the means by which cells respond to extracellular stimuli. Regardless of the nature of the cell surface receptor (e.g. protein tyrosine kinase or seven-transmembrane G-protein coupled), protein kinases and phosphatases along with phopholipases are the essential machinery by which the signal is further transmitted within the cell [Marshall, J. C. Cell, 80, 179–278 (1995)]. Protein kinases can be categorized into five classes with the two major classes being, tyrosine kinases and serine/threonine kinases depending upon whether the enzyme phosphorylates its substrate(s) on specific tyrosine (s) or serine/threonine(s) residues [Hunter, T., Methods in Enzymology (Protein Kinase Classification) p. 3, Hunter, T.; Sefton, B. M.; eds. vol. 200, Academic Press; San Diego, 1991].

For most biological responses, multiple intracellular kinases are involved and an individual kinase can be involved in more than one signaling event. These kinases are often cytosolic and can translocate to the nucleus or the ribosomes where they can affect transcriptional and translational events, respectively. The involvement of kinases in transcriptional control is presently much better understood than their effect on translation as illustrated by the studies on growth factor induced signal transduction involving MAP/ERK kinase [Marshall, C. J. Cell, 80, 179 (1995); Herskowitz, I. Cell 80, 187 (1995); Hunter, T. Cell, 80, 225 (1995); Seger, R., and Krebs, E. G. FASEB J., 726–735 (1995)].

While many signaling pathways are part of cell homeostasis, numerous cytokines (e.g., IL-1 and TNF) and certain other mediators of inflammation (e.g., COX-2, and iNOS) are produced only as a response to stress signals such as bacterial lippopolysaccharide (LPS). The first indications suggesting that the signal transduction pathway leading to LPS-induced cytokine biosynthesis involved protein kinases came from studies of Weinstein [Weinstein, et al., J. Immunol. 151, 3829(1993)] but the specific protein kinases involved were not identified. Working from a similar perspective, Han [Han, et al., Science 265, 808(1994)] identified murine p38 as a kinase which is tyrosine phosphorylated in response to LPS. Definitive proof of the involvement of the p38 kinase in LPS-stimulated signal transduction pathway leading to the initiation of proinflammatory cytokine biosynthesis was provided by the independent discovery of p38 kinase by Lee [Lee; et al., Nature, 372, 739(1994)] as the molecular target for a novel class of anti-inflammatory agents. The discovery of p38 (termed by Lee as CSBP 1 and 2) provided a mechanism of action of a class of anti-inflammatory compounds for which SK&F 86002 was the prototypic example. These compounds inhibited IL-1 and TNF synthesis in human monocytes at concentrations in the low uM range [Lee, et al., Int. J. Immunopharmac. 10(7), 835(1988)] and exhibited activity in animal models which are refractory to cyclooxygenase inhibitors [Lee; et al., Annals N. Y. Acad. Sci., 696, 149 (1993)].

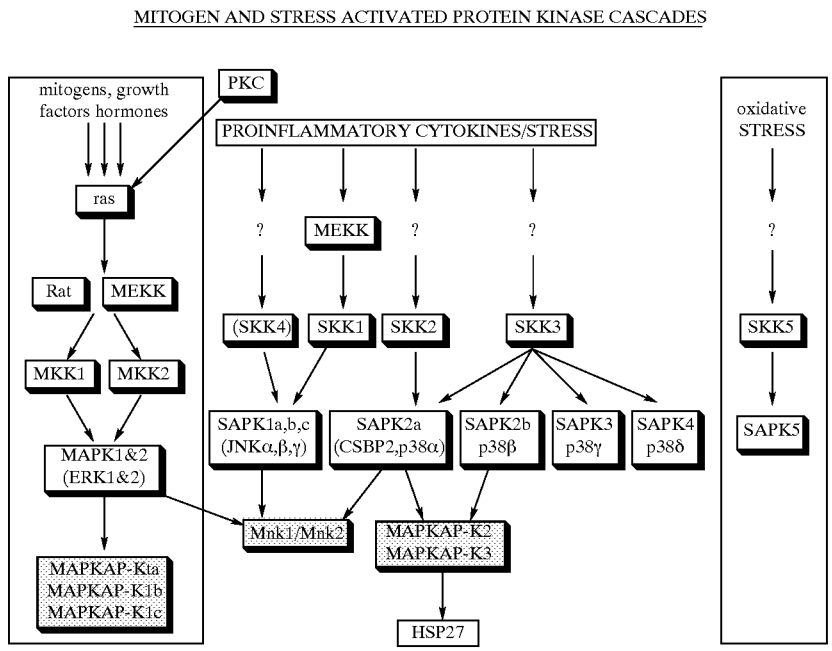

FIG. 1

MITOGEN AND STRESS ACTIVATED PROTEIN KINASE CASCADES

It is now firmly established that CSBP/p38 is a one of several kinases involved in a stress-response signal transduction pathway which is parallel to and largely independent of the analogous mitogen-activated protein kinase (MAP) kinase cascade (FIG. 1). Stress signals, including LPS, pro-inflammatory cytokines, oxidants, UV light and osmotic stress, activate kinases upstream from CSBP/p38 which in turn phosphorylate CSBP/p38 at threonine 180 and tyrosine 182 resulting in CSBP/p38 activation. MAPKAP kinase-2 and MAPKAP kinase-3 have been identified as downstream substrates of CSBP/p38 which in turn phosphorylate heat shock protein Hsp 27 (FIG. 2). It is not yet known whether MAPKAP-2, MAPKAP-3, Mnk1 or Mnk2 are involved in cytokine biosynthesis or alternatively that inhibitors of CSBP/p38 kinase might regulate cytokine biosynthesis by blocking a yet unidentified substrate downstream from CSBP/p38 [Cohen, P. *Trends Cell Biol.*, 353–361(1997)].

p38 Kinase Pathway

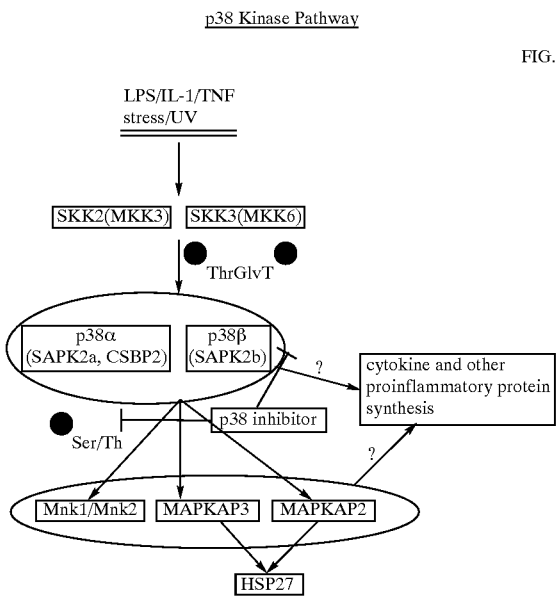

FIG. 2

What is known, however, is that in addition to inhibiting IL-1 and TNF, CSBP/p38 kinase inhibitors (SK&F 86002 and SB 203580) also decrease the synthesis of a wide variety of pro-inflammatory proteins including, IL-6, IL-8, GM-CSF and COX-2. Inhibitors of CSBP/p38 kinase have also been shown to suppress the TNF-induced expression of VCAM-1 on endothelial cells, the TNF-induced phosphorylation and activation of cytosolic $PLA_2$ and the IL-1-stimulated synthesis of collagenase and stromelysin. These and additional data demonstrate that CSBP/p38 is involved not only cytokine synthesis, but also in cytokine signaling [CSBP/P38 kinase reviewed in Cohen, P. *Trends Cell Biol.*, 353–361(1997)].

Interleukin-1 (IL-1) and Tumor Necrosis Factor (TNF) are biological substances produced by a variety of cells, such as monocytes or macrophages. IL-1 has been demonstrated to mediate a variety of biological activities thought to be important in immunoregulation and other physiological conditions such as inflammation [See, e.g., Dinarello et al., Rev. Infect. Disease, 6, 51 (1984)]. The myriad of known biological activities of IL-1 include the activation of T helper cells, induction of fever, stimulation of prostaglandin or collagenase production, neutrophil chemotaxis, induction of acute phase proteins and the suppression of plasma iron levels.

There are many disease states in which excessive or unregulated IL-1 production is implicated in exacerbating and/or causing the disease. These include rheumatoid arthritis, osteoarthritis, endotoxemia and/or toxic shock syndrome, other acute or chronic inflammatory disease states such as the inflammatory reaction induced by endotoxin or inflammatory bowel disease; tuberculosis, atherosclerosis, muscle degeneration, cachexia, psoriatic arthritis, Reiter's syndrome, rheumatoid arthritis, gout, traumatic arthritis, rubella arthritis, and acute synovitis. Recent evidence also links IL-1 activity to diabetes and pancreatic β cells [review of the biological activities which have been attributed to IL-1 Dinarello, *J. Clinical Immunology*, 5 (5), 287–297 (1985)].

Excessive or unregulated TNF production has been implicated in mediating or exacerbating a number of diseases including rheumatoid arthritis, rheumatoid spondylitis, osteoarthritis, gouty arthritis and other arthritic conditions; sepsis, septic shock, endotoxic shock, gram negative sepsis, toxic shock syndrome, adult respiratory distress syndrome, cerebral malaria, chronic pulmonary inflammatory disease, silicosis, pulmonary sarcoisosis, bone resorption diseases, reperfusion injury, graft vs. host reaction, allograft rejections, fever and myalgias due to infection, such as influenza, cachexia secondary to infection or malignancy, cachexia, secondary to acquired immune deficiency syndrome (AIDS), AIDS, ARC (AIDS related complex), keloid formation, scar tissue formation, Crohn's disease, ulcerative colitis, or pyresis.

Interleukin-8 (IL-8) is a chemotactic factor produced by several cell types including mononuclear cells, fibroblasts, endothelial cells, and keratinocytes. Its production from endothelial cells is induced by IL-1, TNF, or lipopolysaccharide (LPS). IL-8 stimulates a number of functions in vitro. It has been shown to have chemoattractant properties for neutrophils, T-lymphocytes, and basophils. In addition it induces histamine release from basophils from both normal and atopic individuals as well as lysozomal enzyme release and respiratory burst from neutrophils. IL-8 has also been shown to increase the surface expression of Mac-1 (CD11b/CD18) on neutrophils without de novo protein synthesis, this may contribute to increased adhesion of the neutrophils to vascular endothelial cells. Many diseases are characterized by massive neutrophil infiltration. Conditions associated with an increased in IL-8 production (which is responsible for chemotaxis of neutrophil into the inflammatory site) would benefit by compounds which are suppressive of IL-8 production.

IL-1 and TNF affect a wide variety of cells and tissues and these cytokines as well as other leukocyte derived cytokines are important and critical inflammatory mediators of a wide variety of disease states and conditions. The inhibition of these cytokines is of benefit in controlling, reducing and alleviating many of these disease states.

Inhibition of signal transduction via CSBP/p38, which in addition to IL-1, TNF and IL-8 described above is also required for the synthesis and/or action of several additional pro-inflammatory proteins (i.e., IL-6, GM-CSF, COX-2, collagenase and stromelysin), is expected to be a highly effective mechanism for regulating the excessive and destructive activation of the immune system. This expectation is supported by the potent and diverse anti-inflammatory activities described for CSBP/p38 kinase inhibitors [Badger, et al., *J. Pharm. Exp. Thera.* 279 (3): 1453–1461.(1996); Griswold, et al, *Pharmacol. Comm.* 7, 323–229 (1996)].

There remains a need for treatment, in this field, for compounds which are cytokine suppressive anti-inflammatory drugs, i.e. compounds which are capable of inhibiting the CSBP/p38/RK kinase.

SUMMARY OF THE INVENTION

This invention relates to the novel compounds of Formula (I), and pharmaceutical compositions comprising a compound of Formula (I), and a pharmaceutically acceptable diluent or carrier.

This invention relates to a method of treating a CSBP/RK/p38 kinase mediated disease, in a mammal in need thereof, which comprises administering to said mammal an effective amount of a compound of Formula (I).

This invention also relates to a method of inhibiting cytokines and the treatment of a cytokine mediated disease, in a mammal in need thereof, which comprises administering to said mammal an effective amount of a compound of Formula (I).

This invention more specifically relates to a method of inhibiting the production of IL-1 in a mammal in need thereof which comprises administering to said mammal an effective amount of a compound of Formula (I).

This invention more specifically relates to a method of inhibiting the production of IL-8 in a mammal in need thereof which comprises administering to said mammal an effective amount of a compound of Formula (I).

This invention more specifically relates to a method of inhibiting the production of TNF in a mammal in need thereof which comprises administering to said mammal an effective amount of a compound of Formula (I).

Accordingly, the present invention provides for a compound of the formula:

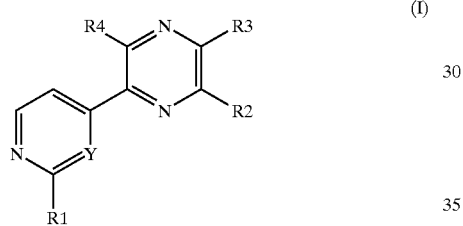

wherein
$R_1$ is hydrogen, X—$R_a$, optionally substituted $C_{1-4}$ alkyl, halogen, hydroxyl, optionally substituted $C_{1-4}$ alkoxy, optionally substituted $C_{1-4}$ alkylthio, optionally substituted $C_{1-4}$ alkylsulfinyl, $CH_2OR_{12}$, amino, mono and di- $C_{1-6}$ alkyl substituted amino, $N(R_{10})C(O)R_b$, $N(R_{10})S(O)_2R_d$, or an N-heterocyclyl ring which ring has from 5 to 7 members and optionally contains an additional heteroatom selected from oxygen, sulfur or $NR_{15}$;

Y is CH or N;

X is oxygen, sulfur or NH;

$R_a$ is $C_{1-6}$ alkyl, aryl, aryl$C_{1-6}$ alkyl, heterocyclic, heterocyclyl$C_{1-6}$ alkyl, heteroaryl, or heteroaryl$C_{1-6}$ alkyl moiety, wherein each of these moieties may be optionally substituted;

$R_b$ is hydrogen, $C_{1-6}$ alkyl, $C_{3-7}$ cycloalkyl, aryl, aryl$C_{1-4}$ alkyl, heteroaryl, heteroaryl$C_{1-4}$ alkyl, heterocyclyl, or heterocyclyl$C1$–4 alkyl;

$R_d$ is $C_{1-6}$ alkyl, $C_{3-7}$ cycloalkyl, aryl, aryl$C_{1-4}$ alkyl, heteroaryl, heteroaryl$C_{1-4}$ alkyl, heterocyclyl, or heterocyclyl$C_{1-4}$ alkyl;

n is 0, or an integer having a value of 1 to 10;

v is 0, or an integer having a value of 1 or 2;

m is 0, or the integer having a value of 1 or 2;

m' is an integer having a value of 1 or 2;

m" is 0, or an integer having a value of 1 to 5;

$R_2$ and $R_3$ are independently hydrogen, $(CR_{10}R_{23})_nOR_9$, $(CR_{10}R_{23})_nOR_{11}$, $C_{1-10}$ alkyl, halo-substituted $C_{1-10}$ alkyl, $C_{2-10}$ alkenyl, $C_{2-10}$ alkynyl, $C_{3-7}$ cycloalkyl, $C_{3-7}$cycloalkyl$C_{1-10}$ alkyl, $C_{5-7}$ cycloalkenyl, $C_{5-7}$ cycloalkenyl $C_{1-10}$ alkyl, aryl, aryl$C_{1-10}$ alkyl, heteroaryl, heteroaryl$C_{1-10}$ alkyl, heterocyclyl, heterocyclyl$C_{1-10}$ alkyl, $(CR_{10}R_{23})_nS(O)_mR_{18}$, $(CR_{10}OR_{23})_nNHS(O)_2R_{18}$, $(CR_{10}R_{23})_nNR_{13}R_{14}$, $(CR_{10}R_{23})_nNO_2$, $(CR_{10}R_{23})_nCN$, $(CR_{10}R_{23})_nS(O)$m'$NR_{13}R_{14}$, $(CR_{10}R_{23})_nC(Z)R_{11}$, $(CR_{10}R_{23})_nOC(Z)R_{11}$, $(CR_{10}R_{23})_nC(Z)OR_{11}$, $(CR_{10}R_{23})_nC(Z)NR_{13}R_{14}$, $(CR_{10}R_{23})_nC(Z)NR_{11}OR_9$, $(CR_{10}R_{23})_nNR_{10}(Z)R_{11}$, $(CR_{10}R_{23})_nNR_{10}C(Z)NR_{13}R_{14}$, $(CR_{10}OR_{23})_nN(OR_6)C(Z)NR_{13}R_{14}$, $(CR_{10}R_{23})_nN(OR_6)C(Z)R_{11}$, $(CR_{10}R_{23})_nC(=NOR_6)R_{11}$, $(CR_{10}R_{23})_nNR_{10}C(=NR_{19})NR_{13}R_{14}$, $(CR_{10}R_{23})_nOC(Z)NR_{13}R_{14}$, $(CR_{10}R_{23})_nNR_{10}(Z)$ $NR_{13}R_{14}$, $(CR_{10}R_{23})_nNR_{10}C(Z)OR_{10}$, 5-($R_{18}$)-1,2,4-oxadizaol-3-yl or 4-($R_{12}$)-5-($R_{18}R_{19}$)-4,5-dihydro-1,2,4-oxadiazol-3-yl; wherein the cycloalkyl, cycloalkylalkyl, aryl, arylalkyl, heteroaryl, heteroaryl alkyl, heterocyclic and heterocyclicalkyl moieties may be optionally substituted;

$R_4$ is phenyl, naphth-1-yl or naphth-2-yl ring, or a heteroaryl ring, which ring is optionally substituted independently by one to three substituents, and which, for a 4-phenyl, 4-naphth-1-yl, 5-naphth-2-yl or 6-naphth-2-yl substituent, is halogen, cyano, nitro, $C(Z)NR_7R_{17}$, $C(Z)OR_{16}$, $(CR_{10}R_{20})_vCOR_{12}$, $SR_5$, $S(O)R_5$, $OR_{12}$, halo-substituted-$C_{1-4}$ alkyl, $C_{1-4}$alkyl, $ZC(Z)R_{12}$, $NR_{10}C(Z)R_{16}$, or $(CR_{10}R_{20})vNR_{10}R_{20}$ and which, for other positions of substitution, is halogen, cyano, nitro, phenyl, $C(Z)NR_{13}R_{14}$, $C(Z)OR_{25}$, $(CR_{10}R_{20})_{m"}COR_{25}$, $S(O)_mR_{25}$, $OR_{25}$, halosubstituted-$C_{1-4}$ alkyl, $C_{1-10}$ alkyl, $ZC(Z)R_{25}$, optionally substituted phenyl, $(CR_{10}R_{20})_{m"}NR_{10}C(Z)R_{25}$, $NR_{10}S(O)_m$, $R_8$, $NR_{10}S(O)_m$, $NR_7R_{17}$, or $(CR_{10}R_{20})_{m"}NR_{13}R_{14}$;

$R_5$ is hydrogen, $C_{1-4}$ alkyl, $C_{2-4}$ alkenyl, $C_{2-4}$ alkynyl or $NR_7R_{17}$, excluding the moieties $SR_5$ being $SNR_7R_{17}$ and $SOR_5$ being SOH;

$R_6$ is hydrogen, a pharmaceutically acceptable cation, $C_{1-10}$ alkyl, $C_{3-7}$ cycloalkyl, aryl, aryl$C_{1-4}$ alkyl, heteroaryl, heteroaryl$C_{1-4}$ alkyl, heterocyclic, aroyl, or $C_{1-10}$ alkanoyl;

$R_7$ and $R_{17}$ is each independently selected from hydrogen or $C_{1-4}$ alkyl or $R_7$ and $R_{17}$ together with the nitrogen to which they are attached form a heterocyclic ring of 5 to 7 members which ring optionally contains an additional heteroatom selected from oxygen, sulfur or $NR_{15}$;

$R_8$ is $C_{1-10}$ alkyl, halo-substituted $C_{1-10}$ alkyl, $C_{2-10}$ alkenyl, $C_{2-10}$alkynyl, $C_{3-7}$ cycloalkyl, $C_{5-7}$ cycloalkenyl, aryl, aryl$C_{1-10}$ alkyl, heteroaryl, heteroaryl$C_{1-10}$ alkyl, $(CR_{10}R_{20})_nOR_{11}$, $(CR_{10}R_{20})_nS$ $(O)_mR_{18}$, $(CR_{10}R_{20})_nNHS(O)_2R_{18}$, or $(CR_{10}R_{20})_n$ $NR_{13}R_{14}$; wherein the aryl, arylalkyl, heteroaryl, heteroaryl alkyl moieties may be optionally substituted;

$R_9$ is hydrogen, $C(Z)R_{11}$ or optionally substituted $C_{1-10}$ alkyl, $S(O)_2R_{18}$, optionally substituted aryl or optionally substituted aryl$C_{1-4}$ alkyl;

$R_{10}$ and $R_{20}$ is each independently selected from hydrogen or $C_{1-4}$ alkyl;

$R_{11}$ is hydrogen, $C_{1-10}$ alkyl, $C_{3-7}$ cycloalkyl, heterocyclyl, heterocyclyl $C_{1-10}$ alkyl, aryl, aryl$C_{1-10}$ alkyl, heteroaryl or a heteroaryl$C_{1-10}$ alkyl moiety, wherein the aryl, arylalkyl, heteroaryl, heteroaryl alkyl, heterocyclyl or heterocyclylalkyl moieties may be optionally substituted;

$R_{12}$ is hydrogen or $R_{16}$;

$R_{13}$ and $R_{14}$ is each independently selected from hydrogen or optionally substituted $C_{1-4}$ alkyl, optionally substituted aryl or optionally substituted aryl-$C_{1-4}$alkyl, or together with the nitrogen which they are attached form a heterocyclic ring of 5 to 7 members which ring optionally contains an additional heteroatom selected from oxygen, sulfur or $NR_9$;

$R_{15}$ is hydrogen, $C_{1-4}$ alkyl or C(Z)—$C_{1-4}$ alkyl;

$R_{16}$ is $C_{1-4}$ alkyl, halo-substituted-$C_{1-4}$ alkyl, or $C_{3-7}$ cycloalkyl;

$R_{18}$ is $C_{1-10}$ alkyl, $C_{3-7}$ cycloalkyl, heterocyclyl, aryl, aryl$C_{1-10}$ alkyl, heterocyclyl, heterocyclyl-$C_{1-10}$ alkyl, heteroaryl or a heteroarylalkyl moiety, wherein the aryl, arylalkyl, heteroaryl, heteroaryl alkyl, heterocyclyl or heterocyclylalkyl moieties may be optionally substituted;

$R_{19}$ is hydrogen, cyano, $C_{1-4}$ alkyl, $C_{3-7}$ cycloalkyl or aryl;

$R_{23}$ is hydrogen, $C_{1-6}$ alkyl, $C_{3-7}$ cycloalkyl, aryl, aryl$C_{1-4}$ alkyl, heteroaryl, heteroaryl$C_{1-4}$ alkyl, heterocyclyl, or heterocyclyl$C_{1-4}$ alkyl moiety, all of which moieties may be optionally substituted;

$R_{25}$ is heterocyclyl, heterocyclyl$C_{1-10}$ alkyl or $R_8$; and

Z is oxygen or sulfur;

or a pharmaceutically acceptable salt thereof.

DETAILED DESCRIPTION OF THE INVENTION

Another aspect of the present invention relates to the novel compounds of Formula (II), and pharmaceutical compositions comprising a compound of Formula (II), and a pharmaceutically acceptable diluent or carrier.

This invention relates to a method of treating a CSBP/RK/p38 kinase mediated disease, in a mammal in need thereof, which comprises administering to said mammal an effective amount of a compound of Formula (II).

This invention also relates to a method of inhibiting cytokines and the treatment of a cytokine mediated disease, in a mammal in need thereof, which comprises administering to said mammal an effective amount of a compound of Formula (II).

This invention more specifically relates to a method of inhibiting the production of IL-1 in a mammal in need thereof which comprises administering to said mammal an effective amount of a compound of Formula (II).

This invention more specifically relates to a method of inhibiting the production of IL-8 in a mammal in need thereof which comprises administering to said mammal an effective amount of a compound of Formula (II).

This invention more specifically relates to a method of inhibiting the production of TNF in a mammal in need thereof which comprises administering to said mammal an effective amount of a compound of Formula (II).

Accordingly, the present invention provides for a compound of the formula:

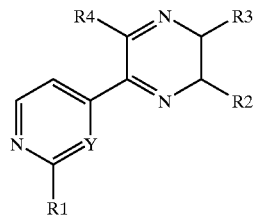

(II)

wherein $R_1$ is hydrogen, X—$R_a$, optionally substituted $C_{1-4}$ alkyl, halogen, hydroxyl, optionally substituted $C_{1-4}$ alkoxy, optionally substituted $C_{1-4}$ alkylthio, optionally substituted $C_{1-4}$ alkylsulfinyl, $CH_2OR_{12}$, amino, mono and di- $C_{1-6}$ alkyl substituted amino, $N(R_{10})C(O)R_b$, $N(R_{10})S(O)_2R_d$, or an N-heterocyclyl ring which ring has from 5 to 7 members and optionally contains an additional heteroatom selected from oxygen, sulfur or $NR_{15}$;

Y is CH or N;

X is oxygen, sulfur or NH;

$R_a$ is $C_{1-6}$ alkyl, aryl, aryl$C_{1-6}$ alkyl, heterocyclic, heterocyclyl$C_{1-6}$ alkyl, heteroaryl, or heteroaryl$C_{1-6}$ alkyl moiety, wherein each of these moieties may be optionally substituted;

$R_b$ is hydrogen, $C_{1-6}$ alkyl, $C_{3-7}$ cycloalkyl, aryl, aryl$C_{1-4}$ alkyl, heteroaryl, heteroaryl$C_{1-4}$ alkyl, heterocyclyl, or heterocyclyl$C_{1-4}$ alkyl;

$R_d$ is $C_{1-6}$ alkyl, $C_{3-7}$ cycloalkyl, aryl, aryl$C_{1-4}$ alkyl, heteroaryl, heteroaryl$C_{1-4}$ alkyl, heterocyclyl, or heterocyclyl$C_{1-4}$ alkyl;

n is 0, or an integer having a value of 1 to 10;

v is 0, or an integer having a value of 1 or 2;

m is 0, or the integer having a value of 1 or 2;

m' is an integer having a value of 1 or 2;

m" is 0, or an integer having a value of 1 to 5;

$R_2$ and $R_3$ are independently hydrogen, $(CR_{10}R_{23})_nOR_9$, $(CR_{10}R_{23})_nOR_{11}$, $C_{1-10}$ alkyl, halo-substituted $C_{1-10}$ alkyl, $C_{2-10}$ alkenyl, $C_{2-10}$ alkynyl, $C_{3-7}$ cycloalkyl, $C_{3-7}$cycloalkyl$C_{1-10}$ alkyl, $C_{5-7}$ cycloalkenyl, $C_{5-7}$ cycloalkenyl $C_{1-10}$ alkyl, aryl, aryl$C_{1-10}$ alkyl, heteroaryl, heteroaryl$C_{1-10}$ alkyl, heterocyclyl, heterocyclyl$C_{1-10}$ alkyl, $(CR_{10}R_{23})_nS(O)_mR_{18}$, $(CR_{10}R_{23})_nNHS(O)_2R_{18}$, $(CR_{10}R_{23})_nNR_{13}R_{14}$, $(CR_{10}R_{23})_nNO_2$, $(CR_{10}R_{23})_nCN$, $(CR_{10}R_{23})_nS(O)_m'NR_{13}R_{14}$, $(CR_{10}R_{23})_nC(Z)R_{11}$, $(CR_{10}R_{23})_nOC(Z)R_{11}$, $(CR_{10}R_{23})_nC(Z)OR_{11}$, $(CR_{10}R_{23})_nC(Z)NR_{13}R_{14}$, $(CR_{10}R_{23})_nC(Z)NR_{11}OR_9$, $(CR_{10}R_{23})_nNR_{10}C(Z)R_{11}$, $(CR_{10}R_{23})_nNR_{10}C(Z)NR_{13}R_{14}$, $(CR_{10}R_{23})_nN(OR_6)C(Z)NR_{13}R_{14}$, $(CR_{10}R_{23})_nN(OR_6)C(Z)R_{11}$, $(CR_{10}R_{23})_nC(=NOR_6)R_{11}$, $(CR_{10}R_{23})_nNR_{10}C(=NR_{19})NR_{13}R_{14}$, $(CR_{10}R_{23})_nOC(Z)NR_{13}R_{14}$, $(CR_{10}R_{23})_nNR_{10}C(Z)NR_{13}R_{14}$, $(CR_{10}R_{23})_nNR_{10}C(Z)OR_{10}$, 5-($R_{18}$)-1,2,4-oxadizaol-3-yl or 4-($R_{12}$)-5-($R_{18}R_{19}$)-4,5-dihydro-1,2,4-oxadiazol-3-yl; wherein the cycloalkyl, cycloalkyl alkyl, aryl, arylalkyl, heteroaryl, heteroaryl alkyl, heterocyclic and heterocyclic alkyl moieties may be optionally substituted;

$R_4$ is phenyl, naphth-1-yl or naphth-2-yl ring, or a heteroaryl ring, which ring is optionally substituted independently by one to three substituents, and which, for a 4-phenyl, 4-naphth-1-yl, 5-naphth-2-yl or 6-naphth-2-yl substituent, is halogen, cyano, nitro, C(Z)NR$_7$R$_{17}$, $C(Z)OR_{16}$, $(CR_{10}R_{20})_vCOR_{12}$, $SR_5$, $S(O)R_5$, $OR_{12}$, halo-substituted-$C_{1-4}$ alkyl, $C_{1-4}$alkyl, $ZC(Z)R_{12}$, $NR_{10}C(Z)R_{16}$, or $(CR_{10}R_{20})vNR_{10}R_{20}$ and which, for other positions of substitution, is halogen, cyano, nitro, phenyl, $C(Z)NR_{13}R_{14}$, $C(Z)OR_{25}$, $(CR_{10}OR_{20})_{m''}$ $COR_{25}$, $S(O)_mR_{25}$, $OR_{25}$, halosubstituted-$C_{1-4}$ alkyl, $C_{1-10}$ alkyl, $ZC(Z)R_{25}$, optionally substituted phenyl, $(CR_{10}R_{20})_{m''}NR_{10}C(Z)R_{25}$, $NR_{10}S(O)_m$'$R_8$, $NR_{10}S(O)_m$'$NR_7R_{17}$, or $(CR_{10}R_{20})_{m''}NR_{13}R_{14}$;

$R_5$ is hydrogen, $C_{1-4}$ alkyl, $C_{2-4}$ alkenyl, $C_{2-4}$ alkynyl or $NR_7R_{17}$, excluding the moieties $SR_5$ being $SNR_7R_{17}$ and $SOR_5$ being SOH;

$R_6$ is hydrogen, a pharmaceutically acceptable cation, $C_{1-10}$ alkyl, $C_{3-7}$ cycloalkyl, aryl, aryl$C_{1-4}$ alkyl, heteroaryl, heteroaryl$C_{1-4}$ alkyl, heterocyclic, aroyl, or $C_{1-10}$ alkanoyl;

$R_7$ and $R_{17}$ is each independently selected from hydrogen or $C_{1-4}$ alkyl or $R_7$ and $R_{17}$ together with the nitrogen to which they are attached form a heterocyclic ring of 5 to 7 members which ring optionally contains an additional heteroatom selected from oxygen, sulfur or $NR_{15}$;

$R_8$ is $C_{1-10}$ alkyl, halo-substituted $C_{1-10}$ alkyl, $C_{2-10}$ alkenyl, $C_{2-10}$ alkynyl, $C_{3-7}$ cycloalkyl, $C_{5-7}$ cycloalkenyl, aryl, aryl$C_{1-10}$ alkyl, heteroaryl, heteroaryl$C_{1-10}$ alkyl, $(CR_{10}R_{20})_nOR_{11}$, $(CR_{10}R_{20})_nS(O)_mR_{18}$, $(CR_{10}R_{20})_nNHS(O)_2R_{18}$, or $(CR_{10}R_{20})_nNR_{13}R_{14}$; wherein the aryl, arylalkyl, heteroaryl, heteroaryl alkyl moieties may be optionally substituted;

$R_9$ is hydrogen, $C(Z)R_{11}$ or optionally substituted $C_{1-10}$ alkyl, $S(O)_2R_{18}$, optionally substituted aryl or optionally substituted aryl$C_{1-4}$ alkyl;

$R_{10}$ and $R_{20}$ is each independently selected from hydrogen or $C_{1-4}$ alkyl;

$R_{11}$ is hydrogen, $C_{1-10}$ alkyl, $C_{3-7}$ cycloalkyl, heterocyclyl, heterocyclyl $C_{1-10}$ alkyl, aryl, aryl$C_{1-10}$ alkyl, heteroaryl or a heteroaryl$C_{1-10}$ alkyl moiety, wherein the aryl, arylalkyl, heteroaryl, heteroaryl alkyl, heterocyclyl or heterocyclylalkyl moieties may be optionally substituted;

$R_{12}$ is hydrogen or $R_{16}$;

$R_{13}$ and $R_{14}$ is each independently selected from hydrogen or optionally substituted $C_{1-4}$ alkyl, optionally substituted aryl or optionally substituted aryl-$C_{1-4}$alkyl, or together with the nitrogen which they are attached form a heterocyclic ring of 5 to 7 members which ring optionally contains an additional heteroatom selected from oxygen, sulfur or $NR_9$;

$R_{15}$ is hydrogen, $C_{1-4}$ alkyl or $C(Z)$—$C_{1-4}$ alkyl;

$R_{16}$ is $C_{1-4}$ alkyl, halo-substituted-$C_{1-4}$ alkyl, or $C_{3-7}$ cycloalkyl;

$R_{18}$ is $C_{1-10}$ alkyl, $C_{3-7}$ cycloalkyl, heterocyclyl, aryl, aryl$C_{1-10}$ alkyl, heterocyclyl, heterocyclyl-$C_{1-10}$ alkyl, heteroaryl or a heteroarylalkyl moiety, wherein the aryl, arylalkyl, heteroaryl, heteroaryl alkyl, heterocyclyl or heterocyclylalkyl moieties may be optionally substituted;

$R_{19}$ is hydrogen, cyano, $C_{1-4}$ alkyl, $C_{3-7}$ cycloalkyl or aryl;

$R_{23}$ is hydrogen, $C_{1-6}$ alkyl, $C_{3-7}$ cycloalkyl, aryl, aryl$C_{1-4}$ alkyl, heteroaryl, heteroaryl$C_{1-4}$ alkyl, heterocyclyl, or heterocyclyl$C_{1-4}$ alkyl moiety, all of which moieties may be optionally substituted;

$R_{25}$ is heterocyclyl, heterocyclyl$C_{1-10}$ alkyl or $R_8$; and

Z is oxygen or sulfur;

or a pharmaceutically acceptable salt thereof.

The novel compounds of Formula (I) and (II) herein may also be used in association with the veterinary treatment of mammals, other than humans, in need of inhibition of cytokine inhibition or production. In particular, cytokine mediated diseases for treatment, therapeutically or prophylactically, in animals include disease states such as those noted herein in the Methods of Treatment section, but in particular viral infections. Examples of such viruses include, but are not limited to, lentivirus infections such as, equine infectious anaemia virus, caprine arthritis virus, visna virus, or maedi virus or retrovirus infections, such as but not limited to feline immunodeficiency virus (FIV), bovine immunodeficiency virus, or canine immunodeficiency virus or other retroviral infections.

As can readily be seen from the chemical structure of Formula (I) and (II) the compounds of Formula (II) are the dihydro derivatives of compounds of Formula (I). Therefore, the descriptions of substituent groups as shown herein is the same for compounds of Formula (I) as for compounds of Formula (II), unless specifically indicated.

Therefore, in compounds of Formula (I) and (II), suitable $R_1$ moieties include hydrogen, Y, optionally substituted $C_{1-4}$ alkyl, halogen, hydroxyl, optionally substituted $C_{1-4}$ alkoxy, optionally substituted $C_{1-4}$ alkylthio, optionally substituted $C_{1-4}$ alkylsulfinyl, $CH_2OR_{12}$, amino, mono and di- $C_{1-6}$ alkyl substituted amino, $N(R_{10})C(O)R_b$; $N(R_{10})S(O)_2R_d$; or an N-heterocyclyl ring which ring has from 5 to 7 members and optionally contains an additional heteroatom selected from oxygen, sulfur or $NR_{15}$. Preferably the pyridine or pyrmidine ring is subsituted.

Suitably Y is $X_1$—$R_a$; and $X_1$ is oxygen, sulfur, or nitrogen, preferably oxygen.

Suitably, $R_a$ is $C_{1-6}$alkyl, aryl, aryl$C_{1-6}$alkyl, heterocyclic, heterocyclyl$C_{1-6}$ alkyl, heteroaryl, or heteroaryl$C_{1-6}$alkyl, wherein each of these moieties may be optionally substituted as defined herein.

When the substituent is contains the $R_a$ moiety, and $R_a$ is aryl, it is preferably phenyl or naphthyl. When $R_a$ is an aryl alkyl, it is preferably benzyl or napthylmethyl. When $R_a$ is heterocyclic or heterocyclic alkyl moiety, the heterocyclic portion is preferably pyrrolindinyl, piperidine, morpholino, tetrahydropyran, tetrahydrothiopyranyl, tetrahydrothio-pyran-sulfinyl, tetrahydrothio-pyransulfonyl, pyrrolindinyl, indole, or piperonyl. It is noted that the heterocyclic rings herein may contain unsaturation, such as in an indole ring. When $R_a$ is a heteroaryl or heteroarylalkyl moiety it is as defined herein.

These $R_a$ aryl, heterocyclic and heteroaryl rings may also be optionally substituted one or more times independently with halogen; $C_{1-4}$ alkyl, such as methyl, ethyl, propyl, isopropyl, or t-butyl; halosubstituted alkyl, such as $CF_3$; hydroxy; hydroxy substituted $C_{1-4}$ alkyl; $C_{1-4}$ alkoxy, such as methoxy or ethoxy; $S(O)_m$alkyl and $S(O)m$ aryl (wherein m is 0, 1, or 2); $C(O)OR_{11}$, such as $C(O)C_{1-4}$ alkyl or $C(O)OH$ moieties; $C(O)R_{11}$; $OC(O)R_c$; O—$(CH_2)_s$—O—, such as in a ketal or dioxyalkylene bridge, and s is 1 to 3; amino; mono- and di- $C_{1-6}$ alkyl substituted amino; $N(R_{10})C(O)R_b$; $N(R_{10})S(O)_2R_d$; $C(O)NR_{10}R_{20}$; $S(O)_2(CR_{10}R_{20})_tNR_{13}R_{14}$ (wherein t is 0, or an integer of 1 to 3); cyano, nitro, or an N-heterocyclyl ring which ring has from 5 to 7 members and optionally contains an additional heteroatom selected from oxygen, sulfur or $NR_{15}$; aryl, such as phenyl; an optionally substituted arylalkyl, such as benzyl or phenethyl; aryloxy, such as phenoxy; or arylalkyloxy such as benzyloxy.

Suitably, $R_b$ is hydrogen, $C_{1-6}$ alkyl, $C_{3-7}$ cycloalkyl, aryl, aryl$C_{1-4}$ alkyl, heteroaryl, heteroaryl$C_{1-4}$alkyl, heterocyclyl, or heterocyclyl$C_{1-4}$ alkyl, wherein all of these moieties may be optionally substituted.

Suitably, $R_c$ is hydrogen, optionally substituted $C_{1-6}$ alkyl, $C_{3-7}$ cycloalkyl, aryl, aryl$C_{1-4}$ alkyl, heteroaryl, heteroaryl$C_{1-4}$alkyl, heterocyclyl, or heterocyclyl$C_{1-4}$ alkyl moiety, wherein all of which may be optionally substituted.

Suitably, $R_d$ is $C_{1-6}$ alkyl, $C_{3-7}$ cycloalkyl, aryl, aryl$C_{1-4}$ alkyl, heteroaryl, heteroaryl$C_{1-4}$alkyl, heterocyclyl, or heterocyclyl$C_{1-4}$ alkyl, wherein all of which may be optionally substituted.

When the $R_a$ moiety is an alkyl group it may be optionally substituted as defined herein. Also the alkyl portion of the $R_1$ substituents, the mono- and di-$C_{1-6}$ alkyl amino moieties, may also be halo substituted.

Preferably, the $R_a$ group is an alkyl, such as methyl, an optionally substituted aryl, such as phenyl, or an optionally substituted arylalkyl, such as benzyl.

When the $R_1$ substituent group is $N(R_{10})C(O)$ $R_b$, $R_b$ is preferably a $C_{1-6}$ alkyl; and $R_{10}$ is preferably hydrogen. It is also recognized that all the $R_b$ moieties, in particular the $C_{1-6}$ alkyl group may be optionally substituted, preferably from one to three times as defined herein. Preferably $R_b$ is $C_{1-6}$ alkyl substituted with halogen, such as fluorine, as in trifluoromethyl or trifluroethyl.

Suitably, $R_4$ is phenyl, naphth-1-yl or naphth-2-yl, or a heteroaryl ring. Preferably $R_4$ is a phenyl or naphthyl ring.

Suitably, $R_4$ is optionally substituted by one to three substituents, each of which is independently selected, and which, for a 4-phenyl, 4-naphth-1-yl, 5-naphth-2-yl or 6-naphth-2-yl or heteroaryl substituent, is halogen, cyano, nitro, $C(Z)NR_7R_{17}$, $C(Z)OR_{16}$, $(CR_{10}R_{20})_vCOR_{12}$, $SR_5$, $S(O)R_5$, $OR_{12}$, halo-substituted-$C_{1-4}$ alkyl, $C_{1-4}$alkyl, $ZC(Z)R_{12}$, $NR_{10}C(Z)R_{16}$, or $(CR_{10}R_{20})vNR_{10}R_{20}$ and which, for other positions of substitution, is halogen, cyano, nitro, phenyl, $C(Z)NR_{13}R_{14}$, $C(Z)OR_{25}$, $(CR_{10}R_{20})_{m''}COR_{25}$, $S(O)_mR_{25}$, $OR_{25}$, halosubstituted-$C_{1-4}$ alkyl, $C_{1-10}$ alkyl, $ZC(Z)R_{25}$, optionally substituted phenyl, $(CR_{10}OR_{20})_{m''}NR_{10}C(Z)R_{25}$, $NR_{10}S(O)_{m'}R_8$, $NR_{10}S(O)_{m'}NR_7R_{17}$, or $(CR_{10}R_{20})_{m''}NR_{13}R_{14}$.

Preferably, for the 4-position on the phenyl ring and the naphth-1-yl, the substituents are selected from halogen, $SR_5$, $SOR_5$, $OR_{12}$, $CF_3$, or $(CR_{10}R_{20})_vNR_{10}R_{20}$, and for other positions of substitution on these rings preferred substitution is halogen, $S(O)_mR_{25}$, $OR_{25}$, $CF_3$, $(CR_{10}R_{20})_{m''}NR_{13}R_{14}$, $NR_{10}C(Z)R_{25}$ or $NR_{10}S(O)_{m'}R_8$.

More preferred substituents for the 4-position in the phenyl and naphth-1-yl and on the 5-position in naphth-2-yl include halogen, especially fluoro and chloro, and $SR_5$ and $SOR_5$ wherein $R_5$ is preferably a $C_{1-2}$ alkyl, more preferably methyl; of which the fluoro and chloro is more preferred, and most especially preferred is fluoro.

For all other substituents, in particular for the 3-position in phenyl and naphth-1-yl rings, the substituents are independently selected from halogen, especially fluoro and chloro; $OR_{25}$, especially $C_{1-4}$ alkoxy; $CF_3$, $NR_{10}R_{20}$, such as amino; $NR_{10}C(Z)R_{25}$, especially $NHCO(C_{1-10}$ alkyl); $NR_{10}S(O)_{m'}R_8$, especially $NHSO_2(C_{1-10}$ alkyl); and $SR_{25}$ and $SOR_{25}$ wherein $R_{25}$ is preferably a $C_{1-2}$ alkyl, more preferably methyl.

When the phenyl ring is disubstituted, preferably it is two independent halogen moieties, such as fluoro and chloro, preferably di-chloro and more preferably in the 3,4-position. It is also preferred that for the 3-position of both the $OR_{25}$ and $ZC(Z)R_{25}$ moieties, that the $R_{25}$ may also include hydrogen.

More preferably, the $R_4$ moiety is an unsubstituted or substituted phenyl. When $R_4$ is substituted phenyl it is preferably substituted at the 4-position with fluoro and/or substituted at the 3-position with fluoro, chloro, $C_{1-4}$ alkoxy, methanesulfonamido or acetamido, or $R_4$ is a phenyl di-substituted at the 3,4-position independently with chloro or fluoro, more preferably chloro. Most preferably, $R_4$ is 4-fluorophenyl.

In Formula (I), $R_{25}$ is heterocyclyl, heterocyclyl$C_{1-10}$ alkyl or $R_8$;

In Formula (I), Z is suitably oxygen or sulfur.

Suitably, $R_2$ and $R_3$ are independently selected from hydrogen, $(CR_{10}R_{23})_nOR_9$, $(CR_{10}R_{23})_nOR_{11}$, $C_{1-10}$alkyl, halo-substituted $C_{1-10}$ alkyl, $C_{2-10}$ alkenyl, $C_{2-10}$ alkynyl, $C_{3-7}$ cycloalkyl, $C_{3-7}$cycloalkyl$C_{1-10}$ alkyl, $C_{5-7}$ cycloalkenyl, $C_{5-7}$ cycloalkenyl $C_{1-10}$alkyl, aryl, aryl$C_{1-10}$ alkyl, heteroaryl, heteroaryl$C_{1-10}$alkyl, heterocyclyl, heterocyclyl$C_{1-10}$ alkyl, $(CR_{10}R_{23})_nS(O)_mR_{18}$, $(CR_{10}R_{23})_nNHS(O)_2R_{18}$, $(CR_{10}R_{23})_nNR_{13}R_{14}$, $(CR_{10}R_{23})_nNO_2$, $(CR_{10}R_{23})_nCN$, $(CR_{10}R_{23})_nS(O)_{m'}NR_{13}R_{14}$, $(CR_{10}R_{230})_nC(Z)R_{11}$, $(CR_{10}R_{23})_nOC(Z)R_{11}$, $(CR_{10}R_{23})_nC(Z)OR_{11}$, $(CR_{10}R_{23})_nC(Z)NR_{13}R_{14}$, $(CR_{10}R_{23})_nC(Z)NR_{11}OR_9$, $(CR_{10}R_{23})_nNR_{10}C(Z)R_{11}$, $(CR_{10}R_{23})_nNR_{10}C(Z)NR_{13}R_{14}$, $(CR_{10}R_{23})_nN(OR_6)C(Z)NR_{13}R_{14}$, $(CR_{10}R_{23})_nN(OR_6)C(Z)R_{11}$, $(CR_{10}R_{23})_nC(=NOR_6)R_{11}$, $(CR_{10}R_{23})_nNR_{10}C(=NR_{19})NR_{13}R_{14}$, $(CR_{10}R_{23})_nOC(Z)NR_{13}R_{14}$, $(CR_{10}R_{23})_nNR_{10}C(Z)R_{13}R_{14}$, $(CR_{10}R_{23})_nNR_{10}C(Z)OR_{10}$, 5-$(R_{18})$-1,2,4-oxadizaol-3-yl or 4-$(R_{12})$-5-$(R_{18}R_{19})$-4,5-dihydro-1,2,4-oxadiazol-3-yl; wherein the cycloalkyl, cycloalkylalkyl, aryl, arylalkyl, heteroaryl, heteroaryl alkyl, heterocyclic and heterocyclic alkyl groups may be optionally substituted.

Suitably, $R_{23}$ is hydrogen, $C_{1-6}$ alkyl, $C_{3-7}$ cycloalkyl, aryl, aryl$C_{1-4}$ alkyl, heteroaryl, heteroaryl$C_{1-4}$alkyl, heterocyclyl, or heterocyclyl$C_{1-4}$ alkyl moiety, all of which may be optionally substituted as defined below.

Preferably, $R_2$ and $R_3$ are hydrogen, an optionally substituted heterocyclyl ring, and optionally substituted heterocyclyl$C_{1-10}$ alkyl, an optionally substituted $C_{1-10}$ alkyl, an optionally substituted $C_{3-7}$cycloalkyl, an optionally substituted $C_{3-7}$cycloalkyl $C_{1-10}$ alkyl, $(CR_{10}R_{23})_nC(Z)OR_{11}$ group, $(CR_{10}R_{23})_nNR_{13}R_{14}$, $(CR_{10}R_{23})_nNHS(O)_2R_{18}$, $(CR_{10}R_{23})_nS(O)_mR_{18}$, an optionally substituted aryl; an optionally substituted aryl$C_{1-10}$ alkyl, $(CR_{10}R_{23})_nOR_{11}$, $(CR_{10}R_{23})_nC(Z)R_{11}$, or $(CR_{10}R_{23})_nC(=NOR_6)R_{11}$ group.

Preferably, $R_2$ is selected from hydrogen, $C_{1-10}$ alkyl, optionally substituted heterocyclyl, optionally substituted heterocyclyl$C_{1-10}$ alkyl, $(CR_{10}R_{23})_nNS(O)_2R_{18}$, $(CR_{10}R_{23})_nS(O)_mR_{18}$, aryl$C_{1-10}$ alkyl, $(CR_{10}R_{23})_nNR_{13}R_{14}$, optionally substituted $C_{3-7}$cycloalkyl, or optionally substituted $C_{3-7}$cycloalkyl $C_{1-10}$ alkyl.

When $R_2$ is an optionally substituted heterocyclyl, the ring is preferably a morpholino, pyrrolidinyl, or a piperidinyl group. When the ring is optionally substituted, the substituents may be directly attached to the free nitrogen, such as in the piperidinyl group or pyrrole ring, or on the ring itself. Preferably the ring is a piperidine or pyrrole, more preferably piperidine. The heterocyclyl ring may be optionally substituted one to four times independently by halogen; $C_{1-4}$ alkyl; aryl, such as phenyl; aryl alkyl, such as benzyl —wherein the aryl or aryl alkyl moieties themselves may be optionally substituted (as in the definition section below); $C(O)OR_{11}$, such as the $C(O)C_{1-4}$ alkyl or $C(O)OH$ moieties; $C(O)H$; $C(O)C_{1-4}$ alkyl, hydroxy substituted $C_{1-4}$ alkyl, $C_{1-4}$ alkoxy, $S(O)_mC_{1-4}$ alkyl (wherein m is 0, 1, or 2), $NR_{10}OR_{20}$ (wherein $R_{10}$ and $R_{20}$ are independently hydrogen or $C_{1-4}$alkyl).

Preferably if the ring is a piperidine, the substituents are directly attached on the available nitrogen, i.e. a 1-Formyl- 4-piperidine, 1-benzyl-4-piperidine, 1-methyl-4-piperidine, 1-ethoxycarbonyl-4-piperidine. If the ring is substituted by an alkyl group and the ring is attached in the 4-position, it is preferably substituted in the 2- or 6- position or both, such as 2,2,6,6-tetramethyl-4-piperidine.

When $R_2$ is an optionally substituted heterocyclyl $C_{1-10}$ alkyl group, the ring is preferably a morpholino, pyrrolidinyl, or a piperidinyl group. Preferably this alkyl moiety is from 1 to 4, more preferably 3 or 4, and most preferably 3, such as in a propyl group. Preferred heterocyclic alkyl groups include but are not limited to, morpholino ethyl, morpholino propyl, pyrrolidinyl propyl, and piperidinyl propyl moieties.

When $R_2$ is an optionally substituted $C_{3-7}$cycloalkyl, or an optionally substituted $C_{3-7}$cycloalkyl $C_{1-10}$ alkyl, the cycloalkyl group is preferably a $C_4$ or $C_6$ ring, most preferably a $C_6$ ring, which ring is optionally substituted. The cycloalkyl ring may be optionally substituted one to three times independently by halogen, such as fluorine, chlorine, bromine or iodine; hydroxy; $OC(O)R_b$, $C_{1-10}$ alkoxy, such as methoxy or ethoxy; $S(O)_m$ alkyl, wherein m is 0, 1, or 2, such as methylthio, methylsulfinyl or methylsulfonyl; $S(O)_m$ aryl; cyano, nitro, amino, mono & di-substituted amino, such as in the $NR_7R_{17}$ group, wherein $R_7$ and $R_{17}$ are as defined in Formula (I), or where the $R_7R_{17}$ may cyclize together with the nitrogen to which they are attached to form a 5 to 7 membered ring which optionally includes an additional heteroatom selected from oxygen, sulfur or $NR_{15}$; $N(R_{10})C(O)X_1$ and $X_1$ is $C_{1-4}$ alkyl, aryl or aryl$C_{1-4}$alkyl; $C_{1-10}$ alkyl, such as methyl, ethyl, propyl, isopropyl, or t-butyl; optionally substituted alkyl wherein the substituents are halogen, (such as $CF_3$), hydroxy, nitro, cyano, amino, mono & di-alkyl substituted amino, such as in the $NR_7R_{17}$ group, $S(O)$m alkyl and $S(O)$m aryl, wherein m is 0, 1 or 2; optionally substituted alkylene, such as ethylene or propylene; optionally substituted alkyne, such as ethyne; $C(O)OR_{11}$, such as the free acid or methyl ester derivative; the group $R_e$; $C(O)H$; =O; =N—$OR_{11}$; $N(H)$—OH (or substituted alkyl or aryl derivatives thereof on the nitrogen or the oxime moiety); $N(OR_f)$—$C(O)$—$R_{21}$; an optionally substituted aryl, such as phenyl; an optionally substituted aryl$C_{1-4}$alkyl, such as benzyl of phenethyl; an optionally substituted heterocycle or heterocyclic $C_{1-4}$alkyl, and further these aryl, arylalkyl, heterocyclic, and heterocyclic alkyl moieties are optionally substituted one to two times by halogen, hydroxy, $C_{1-10}$ alkoxy, $S(O)_m$ alkyl, cyano, nitro, amino, mono & di-substituted amino, such as in the $NR_7R_{17}$ group, an alkyl, or an halosubstituted alkyl.

Suitably $R_e$ is a 1,3-dioxyalkylene group of the formula —O—$(CH_2)_s$—O—, wherein s is 1 to 3, preferably s is 2 yielding a 1,3-dioxyethylene moiety, or ketal functionality.

Suitably $R_f$ is hydrogen, a pharmaceutically acceptable cation, aroyl or a $C_{1-10}$ alkanoyl group.

Suitably $R_{21}$ is $NR_{22}R_{24}$; alkyl$_{1-6}$; halosubstituted alkyl$_{1-6}$; hydroxy substituted alkyl$_{1-6}$; alkenyl$_{2-6}$; aryl or heteroaryl optionally substituted by halogen, alkyl$_{1-6}$, halosubstituted alkyl$_{1-6}$, hydroxyl, or alkoxy$_{1-6}$.

Suitably $R_{22}$ is H or alkyl$_{1-6}$.

Suitably $R_{24}$ is H, alkyl$_{1-6}$, aryl, benzyl, heteroaryl, alkyl substituted by halogen or hydroxyl, or phenyl substituted by a member selected from the group consisting of halo, cyano, alkyl$_{1-12}$, alkoxy$_{1-6}$, halosubstituted alkyl$_{1-6}$, alkylthio, alkylsulphonyl, or alkylsulfinyl; or $R_{22}$ and $R_{24}$ may together with the nitrogen to which they are attached form a ring having 5 to 7 members, which members may be optionally replaced by a heteroatom selected from oxygen, sulfur or nitrogen. The ring may be saturated or contain more than one unsaturated bond. Preferably $R_{21}$ is $NR_{22}R_{24}$ and $R_{22}$ and $R_{24}$ are preferably hydrogen.

When the $R_2$ cycloalkyl moiety is substituted by $NR_7R_{17}$ group, or $NR_7R_{17}$ $C_{1-10}$ alkyl group, and the $R_7$ and $R_{17}$ are as defined in Formula (I), the substituent is preferably an amino, amino alkyl, or an optionally substituted pyrrolidinyl moiety.

A preferred position of ring substitution on the C6 cycloalkyl moiety is the 4-position. When the C6 cycloalkyl ring is di-substituted it is preferably di-substituted at the 4 position as $R_{1'}$ and $R^{2'}$. $R^{1'}$ and $R^{2'}$ are independently the optional substituents indicated above for $R_2$. Preferably, $R^{1'}$ and $R^{2'}$ are hydrogen, hydroxy, alkyl, substituted alkyl, optionally substituted alkyne, aryl, arylalkyl, $NR_7R_{17}$, and $N(R_{10})C(O)R_{11}$. Suitably, alkyl is $C_{1-4}$ alkyl, such as methyl, ethyl, or isopropyl; $NR_7R_{17}$ and $NR_7R_{17}$ alkyl, such as amino, methylamino, aminomethyl, aminoethyl; substituted alkyl such as in cyanomethyl, cyanoethyl, nitroethyl, pyrrolidinyl; aryl such as in phenyl; arylalkyl, such as in benzyl; optionally substituted alkyne, such as ethyne or propynyl; or together $R^{1'}$ and $R^{2'}$ are a keto functionality.

In all instances herein where there is an alkenyl or alkynyl moiety as a substituent group, the unsaturated linkage, i.e., the vinylene or acetylene linkage is preferably not directly attached to the nitrogen, oxygen or sulfur moieties, for instance in $OR_3$, or for certain $R_2$ moieties.

Suitable pharmaceutically acceptable salts are well known to those skilled in the art and include basic salts of inorganic and organic acids, such as hydrochloric acid, hydrobromic acid, sulphuric acid, phosphoric acid, methane sulphonic acid, ethane sulphonic acid, acetic acid, malic acid, tartaric acid, citric acid, lactic acid, succinic acid, fumaric acid, maleic acid, benzoic acid, salicylic acid, phenylacetic acid and mandelic acid. In addition, pharmaceutically acceptable salts of compounds of Formula (I) may also be formed with a pharmaceutically acceptable cation, for instance, if a substituent group comprises a carboxy moiety. Suitable pharmaceutically acceptable cations are well known to those skilled in the art and include alkaline, alkaline earth, ammonium and quaternary ammonium cations.

As used herein, "optionally substituted", unless specifically defined, shall mean such groups as halogen, such as fluorine, chlorine, bromine or iodine; hydroxy; hydroxy substituted $C_{1-10}$alkyl; $C_{1-10}$ alkoxy, such as methoxy or ethoxy; $S(O)$m alkyl, wherein m is 0, 1 or 2, such as methylthio, methylsulfinyl or methylsulfonyl; halosubstituted $C_{1-10}$ alkoxy; amino, mono & di-substituted amino, such as in the $NR_7R_{17}$ group; or where the $R_7R_{17}$ may together with the nitrogen to which they are attached cyclize to form a 5 to 7 membered ring which optionally includes an additional heteroatom selected from O/N/S; $C_{1-10}$ alkyl, cycloalkyl, or cycloalkyl alkyl group, such as methyl, ethyl, propyl, isopropyl, t-butyl, etc. or cyclopropyl methyl; halo-substituted $C_{1-10}$ alkyl, such $CF_3$; an optionally substituted aryl, such as phenyl, or an optionally substituted arylalkyl, such as benzyl or phenethyl, wherein these aryl moieties may also be substituted one to three times by halogen; hydroxy; hydroxy substituted alkyl; $C_{1-10}$ alkoxy; $S(O)_m$ alkyl; amino, mono & di-substituted amino, such as in the $NR_7R_{17}$ group; alkyl, or $CF_3$.

The following terms, as used herein, refer to:

"halo" or "halogens", include the halogens: chloro, fluoro, bromo and iodo.

"$C_{1-10}$alkyl" or "alkyl"—both straight and branched chain radicals of 1 to 10 carbon atoms, unless the chain length is otherwise limited, including, but not limited to, methyl, ethyl, n-propyl, iso-propyl, n-butyl, sec-butyl, iso-butyl, tert-butyl, n-pentyl and the like.

"cycloalkyl" is used herein to mean cyclic radicals, preferably of 3 to 8 carbons, including but not limited to cyclopropyl, cyclopentyl, cyclohexyl, and the like.

"cycloalkenyl" is used herein to mean cyclic radicals, preferably of 5 to 8 carbons, which have at least one bond including but not limited to cyclopentenyl, cyclohexenyl, and the like.

"alkenyl" is used herein at all occurrences to mean straight or branched chain radical of 2–10 carbon atoms, unless the chain length is limited thereto, including, but not limited to ethenyl, 1-propenyl, 2-propenyl, 2-methyl-1-propenyl, 1-butenyl, 2-butenyl and the like.

"aryl"—phenyl and naphthyl.

"heteroaryl" (on its own or in any combination, such as "heteroaryloxy", or "heteroaryl alkyl")—a 5–10 membered aromatic ring system in which one or more rings contain one or more heteroatoms selected from the group consisting of N, O or S, such as, but not limited, to pyrrole, pyrazole, furan, thiophene, indole, quinoline, isoquinoline, quinazolinyl, pyridine, pyrimidine, oxazole, thiazole, thiadiazole, triazole, imidazole, or benzimidazole.

"heterocyclic" (on its own or in any combination, such as "heterocyclylalkyl")—a saturated or partially unsaturated 4–10 membered ring system in which one or more rings contain one or more heteroatoms selected from the group consisting of N, O, or S; such as, but not limited to, pyrrolidine, piperidine, piperazine, morpholine, tetrahydropyran, or imidazolidine.

"aralkyl" or "heteroarylalkyl" or "heterocyclicalkyl" is used herein to mean $C_{1-4}$ alkyl as defined above attached to an aryl, heteroaryl or heterocyclic moiety as also defined herein unless otherwise indicate.

"sulfinyl"—the oxide S(O) of the corresponding sulfide, the term "thio" refers to the sulfide, and the term "sulfonyl" refers to the fully oxidized $S(O)_2$ moiety.

"aroyl"—a C(O)Ar, wherein Ar is as phenyl, naphthyl, or aryl alkyl derivative such as defined above, such group include but are note limited to benzyl and phenethyl.

"alkanoyl"—a $C(O)C_{1-10}$ alkyl wherein the alkyl is as defined above.

It is recognized that the compounds of the present invention may exist as stereoisomers, regioisomers, or diastereiomers. These compounds may contain one or more asymmetric carbon atoms and may exist in racemic and optically active forms. All of these compounds are included within the scope of the present invention.

Exemplified compounds of Formula (I) are:
2-(4-Fluorophenyl)-3-(pyridin-4-yl)pyrazine;
2-(6-Methoxy)napthyl-2-yl-3-(4-pyridyl)pyrazine;
2-Napthyl-2-yl-3-(4pyridyl)pyrazine; or a pharmaceutically acceptable salt thereof.

An exemplified compound of Formula (II) is
2,3-Dihydro-5-(4-Fluorophenyl)-3-(pyridin-4-yl)pyrazine; or a pharmaceutically acceptable salt thereof.

Synthetic Methods

The compounds of Formula (I) and (II) may be obtained by applying synthetic procedures, some of which are illustrated in Scheme I below. The synthesis provided for in these Schemes is applicable for producing compounds of Formula (I) or (II) having a variety of different $R_1$, $R_2$, and $R_4$ groups which are reacted, employing optional substituents which are suitably protected, to achieve compatibility with the reactions outlined herein. Subsequent deprotection, in those cases, then affords compounds of the nature generally disclosed. Once the nucleus has been established, further compounds of Formula (I) or (II) may be prepared by applying standard techniques for functional group interconversion all well known in this art.

Compounds of Formula (I) and (II) are pyrazine derivatives which may be readily prepared using procedures well known to those of skill in the art and may be prepared by analogous methods to those indicated herein below.

2-Aryl-3-(2-substituted-pyrimidin-4-yl)pyrazines and 2-Aryl-3-(pyridin-4-yl)pyrazines can be prepared by reacting the corresponding 1-aryl-2-(2-substituted-pyrimidin-4-yl)ethanedione or 1-aryl-2-(pyridin-4-yl)ethanedione with an appropriate 1,2-diamine, such as 1,2-diaminoethane in a suitable solvent such as pyridine to give the corresponding 2,3-dihydropyrazine which can then be oxidized to the pyrazine with a suitable oxidizing agent such as ferric chloride in ethanol as outlined in Scheme 1 below. See Buehler, et al., *J. Org. Chem.* 1955, 20, 1350–1355; and Steel, et al., *J. Organometallic Chem.* 1990, 395, 359–373.

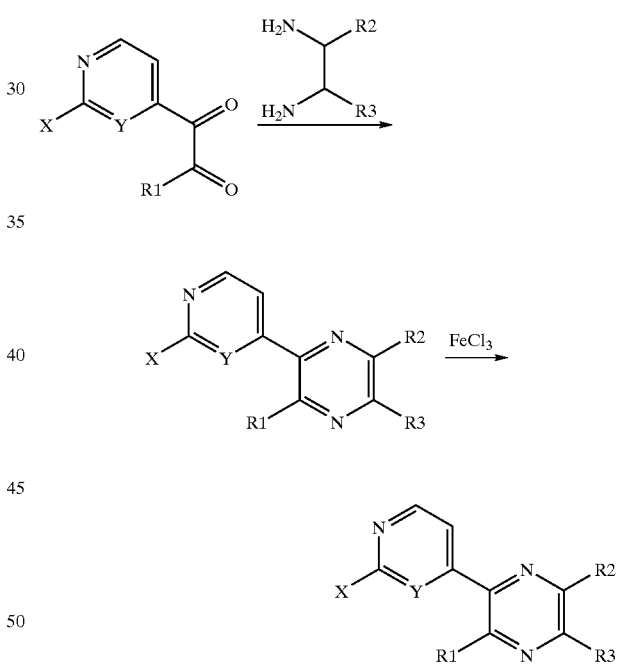

Scheme 1

Alternatively, 2-Aryl-3-(2-substituted-pyrimidin-4-yl)pyrazines and 2-Aryl-3-(pyridin-4-yl)pyrazines can be prepared by reacting an appropriate ketone derivative such as the corresponding oxime of a 1-aryl-2-(2-substituted-pyrimidin-4-yl)ethanedione or 1-aryl-2-(pyridin-4-yl)ethanedione with an appropriate 1,2-diamine, such as 1,2-diaminoethane at elevated temperature in a suitable solvent such as acetic acid to give the corresponding 2,3-dihydropyrazine which can then be oxidized to the corresponding pyrazine with a suitable oxidizing agent such as ferric chloride in ethanol as outlined in Scheme 2 below. See Steel, et al., supra; and Landquist, et al., *J. Chem. Soc.* 1953, 2822–2830.

Scheme 2

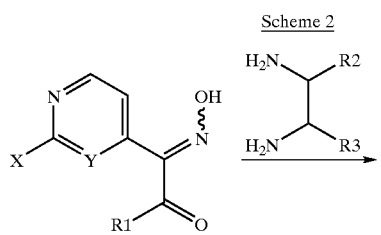

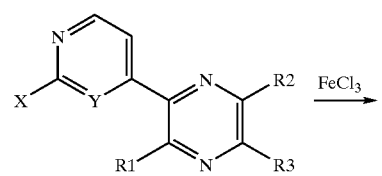

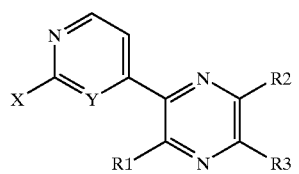

Alternatively 2-Aryl-3-(2-substituted-pyrimidin-4-yl)pyrazines can be prepared as outlined in Scheme 3 below by oxidizing a suitably substituted benzoyl acetate (1) with a suitable oxidizing agent such as selenium dioxide to give the corresponding substituted 2,3-dioxopropionate (2); See Dayer, F. et. al., *Helv. Chim. Acta* 1974, 2201–2209. Reaction of (2) with an appropriate 1,2-diamine such as 1,2-diaminoethane in a suitable solvent such as pyridine gives the corresponding 2,3-dihydropyrazine ester which can then be oxidized to the corresponding pyrazine ester with a suitable oxidizing agent such as ferric chloride in ethanol (3). See Reetz et al., Suk-Hun, *Tett. Lett.*, 1985, 6333–6336. Conversion of ester (3) to the corresponding acid can be accomplished in a variety of ways such as saponification with a suitable base such as sodium hydroxide in a suitable solvent such as aqueous tetrahydrofuran, or by acid hydrolysis with a suitable reagent such as aqueous hydrochloric acid, or by cleavage of an acid labile ester such as a t-butyl ester with trifluoroacetic acid. Conversion of this carboxylic acid to the methyl ketone (4a) can be effected in one step with methyl lithium and protecting the intermediate dilithium salt with TMS-Cl before quenching excess MeLi with HCl under conditions which subsequently removes the TMS groups. See Rubottom, et al., J. Org. Chem., 1983, 48, 1550–1552. Alternatively there are numerous well-established two step procedures wherein the carboxylic acid is first activated and is subsequently then converted to the methyl ketone with a suitable organometallic.

Scheme 3

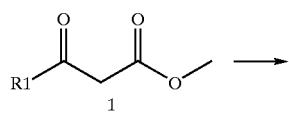

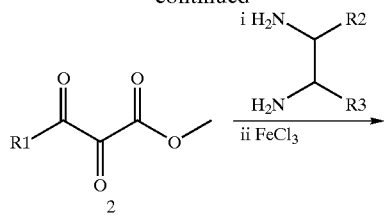

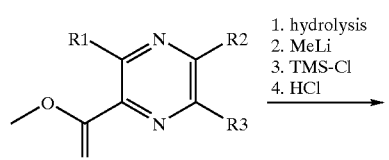

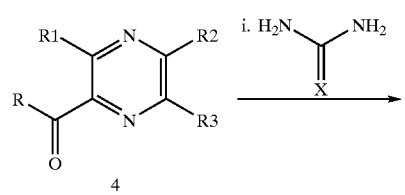

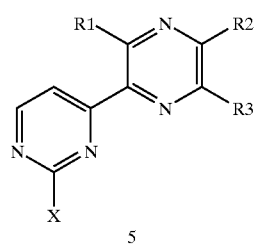

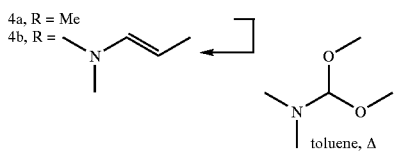

Synthesis of the 3-(pyrimidin-4-yl)pyrazines can then be completed by the method first described by Brederick and co-workers [Bredereck, et. al., *Ber. Dtsch. Chem. Ges.*, 1964, 97, 3397–3406], and subsequently employed to prepare 4-heterocycle substituted pyrimidnes by others. See Sisko, J., *J. Org. Chem.* 1998, 63, 4529–453 1; and Paul, R. et. al., *J. Med. Chem.* 1993, 36, 2716–2725. Thus the methyl ketone (4a-Scheme 3 can be reacted with dimethylformamide dimethyl acetal to form the enamine, (4b-Scheme 3) which is further reacted with urea, thiourea, isothiourea, guanidines, or formamidine to afford pyrimidines (5-Scheme 3) with varied substitution at the 2 position. A method, which has proven effective for synthesis of 2-S-alkyl substituted pyrimidines and used in example 1, involves formation of the 2-thiopyrimidine salt from the enamine and thiourea, in methanolic NaOMe, and capping the salt with alkyl halide. See, Example 1, Adams, J. L. et. al., U.S. Pat. No. 5,716,955 (1998).

A number of the required 1,2-diamino ethanes for use in making compounds of Formula (I) are commercially available. Suitable synthetic routes are readily available in the literature to make the desired intermediate compounds for use herein. A few of these include: conversion of alkenes into primary vicinal aliphatic diamines (Becker, P. N. and Bergman, R. G. *Organometallics* 1983, 2, N 7, 787–796), conversion of amino acids to vicinal diamines (Brunner, Henri et. al. *Eur. J. Med. Chem.*, 1990, 35–44), opening of aziridines with amines (Zygmunt, J. *Tetrahedron* 1985,41, 4979–4982), conversion of vicinal amino alcohols to diamines (Benalil, A et al. *Tetrahedron* 1991, 47), and conversion of nitro olefins to diamines (Imagawa, K et. al. *Chem. Lett.* 1996, 291–292).

Suitable protecting groups for use in the present invention, are well known in the art and described in many references, for instance, Protecting Groups in Organic Synthesis, Greene T W, Wiley-Interscience, New York, 1981.

Pharmaceutically acid addition salts of compounds of formula (I) may be obtained in known manner, for example by treatment thereof with an appropriate amount of acid in the presence of a suitable solvent.

The invention will now be described by reference to the following examples which are merely illustrative and are not to be construed as a limitation of the scope of the present invention.

SYNTHETIC EXAMPLES

The invention will now be described by reference to the following examples which are merely illustrative and are not to be construed as a limitation of the scope of the present invention. All temperatures are given in degrees centigrade, all solvents are highest available purity and all reactions run under anhydrous conditions in an argon atmosphere unless otherwise indicated. Mass spectra were performed upon a VG Zab mass spectrometer using fast atom bombardment, unless otherwise indicated. $^1$H-NMR (hereinafter "NMR") spectra were recorded at 250 MHz using a Bruker AM 250 or Am 400 spectrometer. Multiplicities indicated are: s=singlet, d=doublet, t=triplet, q=quartet, m=multiplet and br indicates a broad signal. Sat. indicates a saturated solution, eq indicates the proportion of a molar equivalent of reagent relative to the principal reactant. Flash chromatography is run over Merck Silica gel 60 (230–400 mesh).

Using synthetic methods as described in the methods section herein, the following compounds have been prepared:

Example 1

2,3-dihydro-5(4-Fluorophenyl)-6-(pyridin-4-yl) pyrazine a) 2,3-dihydro-5(4-Fluorophenyl)-6-(pyridin-4-yl)pyrazine The compound, 1-(4-Fluorophenyl)-2-(pyridin-4-yl) ethanedione, the procedure of which may be found in U.S. Pat. No. 5,656,644, Example 13(b) whose disclosure is incorporated herein by reference in its entirety, (0.2 g, 0.87 mmol), and 1,2-diaminoethane (0.1 g, 1.67 mmol) were dissolved in methylene chloride (1 mL) and stirred under argon at 23° C. for about 12 hours. The solvent was removed in vacuo and the residue was chromatographed on silica gel eluted with 1–3% methanol in methylene chloride. Recrystallization from methylene chloride hexane gave the title compound as an yellow crystalline solid. ES (+) MS m/e= 254 (MH+)

Example 2

2-(4-Fluorophenyl)-3-(pyridin-4-yl)pyrazine a) 2-(4-Fluorophenyl)-3-(pyridin-4-yl)pyrazine The product of example 1a above (0.1 g, 0.4 mmol) was treated with a solution of ferric chloride (0.13 g, 0.8 mmol) in ethanol (1 mL) and stirred at 50° C. for 12 h. The solvent was removed in vacuo and the residue partitioned between ethyl acetate and water. The organic phase dried over anhydrous $Na_2SO_4$, filtered, and evaporated to give the crude product which was chromatographed on silica gel eluted with 1–3% methanol in methylene chloride. Recrystallization from methylene chloride hexane gave the title compound as an white crystalline solid. ES (+) MS m/e=252 (MH+)

Example 3

2-(6-Methoxy)napthyl-2-yl-3-(4-pyridyl)pyrazine a) Preparation of 6-Methoxy-2-naphthoic-N-methoxy-N-methyl amide At 0° C., $SOCl_2$ (1.15 mL, 15.8 mmol) was added very slowly to a stirred solution of 6-methoxy-2-naphthoic acid (2.9 g, 14.3 mmol) in $CH_2Cl_2$ (40 mL) and $Et_3N$(7.9 mL, 57.2 mmol). The solution became dark and homogeneous. After stirring at room temperature for about 40 min., N, O-dimethylhydroxylamine hydrochloride (1.86 g, 17.16 mmol) was added. After the reaction was stirred for 2 hours, it was quenched with water, then extracted with $CH_2Cl_2$ (3×). The organic layer was washed with saturated $Na_2CO_3$ (3×), dried ($Na_2SO_4$), concentrated to afford 2. MS(ES) m/e 246 $[M+H]^+$.

b) Preparation of 6-Methoxynaphth-2-yl-4-pyridylmethyl ketone

At 0° C., n-BuLi (2.5 M in hexane, 8.12 mL, 20.3 mmol) was added to a solution of diisopropylamine (3.32 mL, 23.6 mmol) in THF (20 mL) to generate LDA. The solution was cooled to −78° C., 4-picoline (2.00 mL, 20.3 mmol) was added to the solution, the solution was kept at −78° C., and stirred for 15 min, then the product of Example 3(a) above, (3.65 g, 14.9 mmol) was added. The reaction was warmed to room temperature over 0.5 h, and stirred for another 1 hour. The reaction was quenched by $NH_4Cl$ (5 mL), extracted with $CH_2Cl_2$ (3×). The organic layer was washed with brine, dried ($MgSO_4$), concentrated. The obtained residue was subjected to flash column (from 1%MeOH in $CH_2Cl_2$ to 4% MeOH in $CH_2Cl_2$) to afford the title compound. MS(ES) m/e 278 $[M+H]^+$.

c) Preparation of 2-Hydroxyimino-1-(6-methoxynaphth-2-yl)-2-(4-pyridyl)ethan-1-one $NaNO_2$ (0.27 g, 3.9 mmol) was added to a suspension of the product of Example 3 (b) above, (0.88 g, 3.2 mmol), in 3N HCl (20 mL), and $H_2O$ (20 mL). The slurry was stirred for 3h, filtered, washed with water, air dried to give the title compound. MS(ES) m/e 307 $[M+H]^+$.

d) Preparation of 2-(6-Methoxy)naphth-2-yl-3-(4-pyridyl) pyrazine 5 (SB-422574)

At room temprature under stirring, ethylenediamine (0.027 mL, 0.40 mmol) was added slowly to a solution of step (c) above, (60 mg, 0.20 mmol) in EtOH (7 mL). Then the solution was refluxed for about 6 hours. After cooling, the solution was concentrated, and the residue was chromatographed to give the title compound. MS(ES) m/e 313.4 $[M+H]^+$.

Example 4

2-Napthyl-2-yl-3-(4-pyridyl)pyrazine a) Preparation of 2-Naphthoic-N-methoxy-N-methyl amide At 0° C., $SOCl_2$ (5 mL, 68.5 mmol) was added very slowly to a stirred solution of 2-naphthoic acid (10 g, 58.0 mmol) in $CH_2Cl_2$ (110 mL) and $Et_3N$ (28.3 mL, 203.0 mmol). The solution became dark and homogeneous. After stirring at room temprature for 40 min., N, O-dimethylhydroxylamine hydrochloride (5.85, 60 mmol) was added. After the reaction was stirred for 2 hours, it was quenched with water, then extracted with $CH_2Cl_2$ (3×). The organic layer was washed with saturated Na$_2$CO$_3$ (3×), dried (Na$_2$SO$_4$), concentrated to afford the title compound. MS(ES) m/e 216 [M+H]$^+$.

b) Preparation of 2-Naphthyl-4-pyridylmethyl ketone

At 0° C., n-BuLi (2.5 M in hexane, 2.23 mL, 5.58 mmol) was added to a solution of diisopropylamine (0.91 mL, 6.51 mmol) in THF (20 mL) to generate LDA. The solution was cooled to −78° C., 4-picoline (0.54 mL, 5.58 mmol) was added to the solution, the solution was kept at −78° C., and stirred for 15 min., then the product of Example 4(a) above (1 g, 4.65 mmol) was added. The reaction was warmed to room temperature over 0.5 h, and stirred for about another 1 hour. The reaction was quenched by NH$_4$Cl (5 mL), extracted with CH$_2$Cl$_2$ (3×). The organic layer was washed with brine, dried (MgSO$_4$), concentrated. The obtained residue was subjected to flash column (from 1%MeOH in CH$_2$Cl$_2$ to 4% MeOH in CH$_2$Cl$_2$) to afford the title compound. MS(ES) m/e 248 [M+H]$^+$.

c) Preparation of 2-Hydroxyimino-1-(naphth-2-yl)-2-(4-pyridyl)ethan-1-one

NaNO$_2$ (0.35 g, 5 mmol) was added to a suspension of the product of step (b) above, (0.98 g, 4 mmol), in 3N HCl (20 mL), and H$_2$O (20 mL). The slurry was stirred for 3 hours, filtered, washed with water, air dried to give the title compound. MS(ES) m/e 277 [M+H]$^+$.

d) Preparation of 2-Naphth-2-yl-3-(4-pyridyl)pyrazine

At room temperature under stirring, ethylenediamine (0.1 mL, 1.5 mmol) was added slowly to a solution of steo (c) above, (90 mg, 0.33 mmol) in EtOH (10 mL). Then the solution was refluxed for about 6 hours. After cooling, the solution was concentrated, and the residue was chromatographed to give the title compound. MS(ES) m/e 283 [M+H]$^+$.

Methods of Treatment

The compounds of Formula (I) or (II) or a pharmaceutically acceptable salt thereof can be used in the manufacture of a medicament for the prophylactic or therapeutic treatment of any disease state in a human, or other mammal, which is exacerbated or caused by excessive or unregulated cytokine production by such mammal's cell, such as but not limited to monocytes and/or macrophages.

As used herein, unless specifically indicated, compounds of Formula (I) also refers to and includes compounds of Formula (II).

Compounds of Formula (I) are capable of inhibiting proinflammatory cytokines, such as IL-1, IL-6, IL-8 and TNF and are therefore of use in therapy. IL-1, IL-6, IL-8 and TNF affect a wide variety of cells and tissues and these cytokines, as well as other leukocyte-derived cytokines, are important and critical inflammatory mediators of a wide variety of disease states and conditions. The inhibition of these pro-inflammatory cytokines is of benefit in controlling, reducing and alleviating many of these disease states.

Accordingly, the present invention provides a method of treating a cytokine-mediated disease which comprises administering an effective cytokine-interfering amount of a compound of Formula (I) or a pharmaceutically acceptable salt thereof.

In particular, compounds of Formula (I) or a pharmaceutically acceptable salt thereof are of use in the prophylaxis or therapy of any disease state in a human, or other mammal, which is exacerbated by or caused by excessive or unregulated IL-1, IL-8 or TNF production by such mammal's cell, such as, but not limited to, monocytes and/or macrophages.

Accordingly, in another aspect, this invention relates to a method of inhibiting the production of IL-1 in a mammal in need thereof which comprises administering to said mammal an effective amount of a compound of Formula (I) or a pharmaceutically acceptable salt thereof.

There are many disease states in which excessive or unregulated IL-1 production is implicated in exacerbating and/or causing the disease. These include rheumatoid arthritis, osteoarthritis, meningitis, ischemic and hemorrhagic stroke, neurotrauma/closed head injury, stroke, endotoxemia and/or toxic shock syndrome, other acute or chronic inflammatory disease states such as the inflammatory reaction induced by endotoxin or inflammatory bowel disease, tuberculosis, atherosclerosis, muscle degeneration, multiple sclerosis, cachexia, bone resorption, psoriatic arthritis, Reiter's syndrome, rheumatoid arthritis, gout, traumatic arthritis, rubella arthritis and acute synovitis. Recent evidence also links IL-1 activity to diabetes, pancreatic β cell diseases and Alzheimer's disease.

Use of a CSAID for the treatment of CSBP mediated disease states, can include, but not be limited to neurodegenerative diseases, such as Alzheimer's disease (as noted above), Parkinson's disease and multiple sclerosis, etc.

In a further aspect, this invention relates to a method of inhibiting the production of TNF in a mammal in need thereof which comprises administering to said mammal an effective amount of a compound of Formula (I) or a pharmaceutically acceptable salt thereof.

Excessive or unregulated TNF production has been implicated in mediating or exacerbating a number of diseases including rheumatoid arthritis, rheumatoid spondylitis, osteoarthritis, gouty arthritis and other arthritic conditions, sepsis, septic shock, endotoxic shock, gram negative sepsis, toxic shock syndrome, adult respiratory distress syndrome, chronic pulmonary inflammatory disease and chronic obstructuve pulmonary disease, silicosis, pulmonary sarcoisosis, bone resorption diseases, such as osteoporosis, cardiac, brain and renal reperfusion injury, graft vs. host reaction, allograft rejections, fever and myalgias due to infection, such as influenza, brain infections including encephalitis (including HIV-induced forms), cerebral malaria, meningitis, ischemic and hemorrhagic stroke, cachexia secondary to infection or malignancy, cachexia secondary to acquired immune deficiency syndrome (AIDS), AIDS, ARC (AIDS related complex), keloid formation, scar tissue formation, inflammatory bowel disease, Crohn's disease, ulcerative colitis and pyresis.

Compounds of Formula (I) are also useful in the treatment of viral infections, where such viruses are sensitive to upregulation by TNF or will elicit TNF production in vivo. The viruses contemplated for treatment herein are those that produce TNF as a result of infection, or those which are sensitive to inhibition, such as by decreased replication, directly or indirectly, by the TNF inhibiting-compounds of Formula (I). Such viruses include, but are not limited to HIV-1, HIV-2 and HIV-3, Cytomegalovirus (CMV), Influenza, adenovirus and the Herpes group of viruses, such as but not limited to, Herpes Zoster and Herpes Simplex. Accordingly, in a further aspect, this invention relates to a method of treating a mammal afflicted with a human immunodeficiency virus (HIV) which comprises administering to such mammal an effective TNF inhibiting amount of a compound of Formula (I) or a pharmaceutically acceptable salt thereof.

It is also recognized that both IL-6 and IL-8 are produced during rhinovirus (HRV) infections and contribute to the pathogenesis of common cold and exacerbation of asthma associated with HRV infection (Turner et al. (1998), Clin. Infec. Dis., Vol 26, p 840; Teren et al. (1997), Am J Respir Crit Care Med vol 155, p1362; Grunberg et al. (1997), Am J Respir Crit Care Med 156:609 and Zhu et al, J Clin Invest (1996), 97:421). It has also been demonstrated in vitro that infection of pulmonary epithelial cells with HRV results in production of IL-6 and IL-8 (Subauste et al., J. Clin. Invest. 1995, 96:549.) Epithelial cells represent the primary site of infection of HRV. Therefore another aspect of the present invention is a method of treatment to reduce inflammation associated with a rhinovirus infection, not necessarily a direct effect on virus itself.

Compounds of Formula (I) may also be used in association with the veterinary treatment of mammals, other than in humans, in need of inhibition of TNF production. TNF mediated diseases for treatment, therapeutically or prophylactically, in animals include disease states such as those noted above, but in particular viral infections. Examples of such viruses include, but are not limited to, lentivirus infections such as, equine infectious anaemia virus, caprine arthritis virus, visna virus, or maedi virus or retrovirus infections, such as but not limited to feline immunodeficiency virus (FIV), bovine immunodeficiency virus, or canine immunodeficiency virus or other retroviral infections.

The compounds of Formula (I) may also be used topically in the treatment or prophylaxis of topical disease states mediated by or exacerbated by excessive cytokine production, such as by IL-1 or TNF respectively, such as inflamed joints, eczema, contact dermititis, psoriasis and other inflammatory skin conditions such as sunburn; inflammatory eye conditions including conjunctivitis; pyresis, pain and other conditions associated with inflammation.

Compounds of Formula (I) have also been shown to inhibit the production of IL-8 (Interleukin-8, NAP). Accordingly, in a further aspect, this invention relates to a method of inhibiting the production of IL-8 in a mammal in need thereof which comprises administering to said mammal an effective amount of a compound of Formula (I) or a pharmaceutically acceptable salt thereof.

There are many disease states in which excessive or unregulated IL-8 production is implicated in exacerbating and/or causing the disease. These diseases are characterized by massive neutrophil infiltration such as, psoriasis, inflammatory bowel disease, asthma, cardiac, brain and renal reperfusion injury, adult respiratory distress syndrome, thrombosis and glomerulonephritis. All of these diseases are associated with increased IL-8 production which is responsible for the chemotaxis of neutrophils into the inflammatory site. In contrast to other inflammatory cytokines (IL-1, TNF, and IL-6), IL-8 has the unique property of promoting neutrophil chemotaxis and activation. Therefore, the inhibition of IL-8 production would lead to a direct reduction in the neutrophil infiltration.

The compounds of Formula (I) are administered in an amount sufficient to inhibit cytokine, in particular IL-1, IL-6, IL-8 or TNF, production such that it is regulated down to normal levels, or in some case to subnormal levels, so as to ameliorate or prevent the disease state. Abnormal levels of IL-1, IL-6, IL-8 or TNF, for instance in the context of the present invention, constitute: (i) levels of free (not cell bound) IL-1, IL-6, IL-8 or TNF greater than or equal to 1 picogram per ml; (ii) any cell associated IL-1, IL-6, IL-8 or TNF; or (iii) the presence of IL-1, IL-6, IL-8 or TNF mRNA above basal levels in cells or tissues in which IL-1, IL-6, IL-8 or TNF, respectively, is produced.

The discovery that the compounds of Formula (I) are inhibitors of cytokines, specifically IL-1, IL-6, IL-8 and TNF is based upon the effects of the compounds of Formulas (I) on the production of the IL-1, IL-8 and TNF in in vitro assays which are described herein.

As used herein, the term "inhibiting the production of IL-1 (IL-6, IL-8 or TNF)" refers to:
a) a decrease of excessive in vivo levels of the cytokine (IL-1, IL-6, IL-8 or TNF) in a human to normal or sub-normal levels by inhibition of the in vivo release of the cytokine by all cells, including but not limited to monocytes or macrophages;
b) a down regulation, at the genomic level, of excessive in vivo levels of the cytokine (IL-1, IL-6, IL-8 or TNF) in a human to normal or sub-normal levels;
c) a down regulation, by inhibition of the direct synthesis of the cytokine (IL-1, IL-6, IL-8 or TNF) as a postranslational event; or
d) a down regulation, at the translational level, of excessive in vivo levels of the cytokine (IL-1, IL-6, IL-8 or TNF) in a human to normal or sub-normal levels.

As used herein, the term "TNF mediated disease or disease state" refers to any and all disease states in which TNF plays a role, either by production of TNF itself, or by TNF causing another monokine to be released, such as but not limited to IL-1, IL-6 or IL-8. A disease state in which, for instance, IL-1 is a major component, and whose production or action, is exacerbated or secreted in response to TNF, would therefore be considered a disease stated mediated by TNF.

As used herein, the term "cytokine" refers to any secreted polypeptide that affects the functions of cells and is a molecule which modulates interactions between cells in the immune, inflammatory or hematopoietic response. A cytokine includes, but is not limited to, monokines and lymphokines, regardless of which cells produce them. For instance, a monokine is generally referred to as being produced and secreted by a mononuclear cell, such as a macrophage and/or monocyte. Many other cells however also produce monokines, such as natural killer cells, fibroblasts, basophils, neutrophils, endothelial cells, brain astrocytes, bone marrow stromal cells, epideral keratinocytes and B-lymphocytes. Lymphokines are generally referred to as being produced by lymphocyte cells. Examples of cytokines include, but are not limited to, Interleukin-1 (IL-1), Interleukin-6 (IL-6), Interleukin-8 (IL-8), Tumor Necrosis Factor-alpha (TNF-α) and Tumor Necrosis Factor beta (TNF-β).

As used herein, the term "cytokine interfering" or "cytokine suppressive amount" refers to an effective amount of a compound of Formula (I) which will cause a decrease in the in vivo levels of the cytokine to normal or sub-normal levels, when given to a patient for the prophylaxis or treatment of a disease state which is exacerbated by, or caused by, excessive or unregulated cytokine production.

As used herein, the cytokine referred to in the phrase "inhibition of a cytokine, for use in the treatment of a HIV-infected human" is a cytokine which is implicated in (a) the initiation and/or maintenance of T cell activation and/or activated T cell-mediated HIV gene expression and/or replication and/or (b) any cytokine-mediated disease associated problem such as cachexia or muscle degeneration.

As TNF-β (also known as lymphotoxin) has close structural homology with TNF-α (also known as cachectin) and since each induces similar biologic responses and binds to the same cellular receptor, both TNF-α and TNF-β are inhibited by the compounds of the present invention and thus are herein referred to collectively as "TNF" unless specifically delineated otherwise.

A member of the MAP kinase family, alternatively termed CSBP, p38, or RK, has been identified independently by several laboratories [See Lee et al., Nature, Vol. 300 n(72), 739–746 (1994)]. Activation of this novel protein kinase via dual phosphorylation has been observed in different cell systems upon stimulation by a wide spectrum of stimuli, such as physicochemical stress and treatment with lipopolysaccharide or proinflammatory cytokines such as interleukin-1 and tumor necrosis factor. The cytokine biosynthesis inhibitors, of the present invention, compounds of Formula (I), have been determined to be potent and selective inhibitors of CSBP/p38/RK kinase activity. These inhibitors are of aid in determining the signaling pathways involvement in inflammatory responses. In particular, for the first time a definitive signal transduction pathway can be prescribed to the action of lipopolysaccharide in cytokine production in macrophages. In addition to those diseases already noted, treatment of stroke, neurotrauma, cardiac and renal reperfusion injury, thrombosis, glomerulonephritis, diabetes and pancreatic $\beta$ cells, multiple sclerosis, muscle degeneration, eczema, psoriasis, sunburn, and conjunctivitis are also included.

The cytokine inhibitors were subsequently tested in a number of animal models for anti-inflammatory activity. Model systems were chosen that were relatively insensitive to cyclooxygenase inhibitors in order to reveal the unique activities of cytokine suppressive agents. The inhibitors exhibited significant activity in many such in vivo studies. Most notable are its effectiveness in the collagen-induced arthritis model and inhibition of TNF production in the endotoxic shock model. In the latter study, the reduction in plasma level of TNF correlated with survival and protection from endotoxic shock related mortality. Also of great importance are the compounds effectiveness in inhibiting bone resorption in a rat fetal long bone organ culture system. Griswold et al., (1988) *Arthritis Rheum.* 31:1406–1412; Badger, et al., (1989) *Circ. Shock* 27, 51–61; Votta et al., (1994)in vitro. *Bone* 15, 533–538; Lee et al., (1993). B *Ann. N. Y. Acad. Sci.* 696, 149–170.

Another aspect of the present invention is to the novel use of these CSBP/cytokine inhibitors for the treatment of chronic inflammatory or proliferative or angiogenic diseases which are caused by excessive, or inappropriate angiogenesis.

Chronic diseases which have an inappropriate angiogenic component are various ocular neovasularizations, such as diabetic retinopathy and macular degeneration. Other chronic diseases which have an excessive or increased proliferation of vasculature are tumor growth and metastasis, atherosclerosis, and certain arthritic conditions. Atherosclerosis as a disease may also include transplant graft induced atheroschierosis. Therefore cytokine inhibitors will be of utility in the blocking of the angiogenic component of these disease states.

The term "excessive or increased proliferation of vasculature inappropriate angiogenesis" as used herein includes, but is not limited to, diseases which are characterized by hemangiomas and ocular diseases.

The term "inappropriate angiogenesis" as used herein includes, but is not limited to, diseases which are characterized by vesicle proliferation with accompanying tissue proliferation, such as occurs in cancer, metastasis, arthritis and atherosclerosis.

In order to use a compound of Formula (I) or a pharmaceutically acceptable salt thereof in therapy, it will normally be Formulated into a pharmaceutical composition in accordance with standard pharmaceutical practice. This invention, therefore, also relates to a pharmaceutical composition comprising an effective, non-toxic amount of a compound of Formula (I) and a pharmaceutically acceptable carrier or diluent.

Compounds of Formula (I), pharmaceutically acceptable salts thereof and pharmaceutical compositions incorporating such may conveniently be administered by any of the routes conventionally used for drug administration, for instance, orally, topically, parenterally or by inhalation. The compounds of Formula (I) may be administered in conventional dosage forms prepared by combining a compound of Formula (I) with standard pharmaceutical carriers according to conventional procedures. The compounds of Formula (I) may also be administered in conventional dosages in combination with a known, second therapeutically active compound. These procedures may involve mixing, granulating and compressing or dissolving the ingredients as appropriate to the desired preparation. It will be appreciated that the form and character of the pharmaceutically acceptable character or diluent is dictated by the amount of active ingredient with which it is to be combined, the route of administration and other well-known variables. The carrier(s) must be "acceptable" in the sense of being compatible with the other ingredients of the formulation and not deleterious to the recipient thereof.

The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like. Similarly, the carrier or diluent may include time delay material well known to the art, such as glyceryl mono-stearate or glyceryl distearate alone or with a wax.

A wide variety of pharmaceutical forms can be employed. Thus, if a solid carrier is used, the preparation can be tableted, placed in a hard gelatin capsule in powder or pellet form or in the form of a troche or lozenge. The amount of solid carrier will vary widely but preferably will be from about 25 mg. to about 1 g. When a liquid carrier is used, the preparation will be in the form of a syrup, emulsion, soft gelatin capsule, sterile injectable liquid such as an ampule or nonaqueous liquid suspension.

Compounds of Formula (I) may be administered topically, that is by non-systemic administration. This includes the application of a compound of Formula (I) externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Formulations suitable for topical administration include liquid or semi-liquid preparations suitable for penetration through the skin to the site of inflammation such as liniments, lotions, creams, ointments or pastes, and drops suitable for administration to the eye, ear or nose. The active ingredient may comprise, for topical administration, from 0.001% to 10% w/w, for instance from 1% to 2% by weight of the formulation. It may however comprise as much as 10% w/w but preferably will comprise less than 5% w/w, more preferably from 0.1% to 1% w/w of the formulation.

Lotions according to the present invention include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil.

Creams, ointments or pastes according to the present invention are semi-solid formulations of the active ingredient for external application. They may be made by mixing the active ingredient in finely-divided or powdered form, alone or in solution or suspension in an aqueous or non-aqueous fluid, with the aid of suitable machinery, with a greasy or non-greasy base. The base may comprise hydrocarbons such as hard, soft or liquid paraffin, glycerol, beeswax, a metallic soap; a mucilage; an oil of natural origin such as almond, corn, arachis, castor or olive oil: wool fat or its derivatives or a fatty acid such as steric or oleic acid together with an alcohol such as propylene glycol or a macrogel. The formulation may incorporate any suitable surface active agent such as an anionic, cationic or non-ionic surfactant such as a sorbitan ester or a polyoxyethylene derivative thereof. Suspending agents such as natural gums. cellulose derivatives or inorganic materials such as silicaceous silicas, and other ingredients such as lanolin, may also be included.

Drops according to the present invention may comprise sterile aqueous or oily solutions or suspensions and may be prepared by dissolving the active ingredient in a suitable aqueous solution of a bactericidal and/or fungicidal agent and/or any other suitable preservative, and preferably including a surface active agent. The resulting solution may then be clarified by filtration, transferred to a suitable container which is then sealed and sterilized by autoclaving or maintaining at 98–100° C. for half an hour. Alternatively, the solution may be sterilized by filtration and transferred to the container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Compounds of formula (I) may be administered parenterally, that is by intravenous, intramuscular, subcutaneous intranasal, intrarectal, intravaginal or intraperitoneal administration. The subcutaneous and intramuscular forms of parenteral administration are generally preferred. Appropriate dosage forms for such administration may be prepared by conventional techniques. Compounds of Formula (I) may also be administered by inhalation, that is by intranasal and oral inhalation administration. Appropriate dosage forms for such administration, such as an aerosol formulation or a metered dose inhaler, may be prepared by conventional techniques.

For all methods of use disclosed herein for the compounds of Formula (I), the daily oral dosage regimen will preferably be from about 0.1 to about 80 mg/kg of total body weight, preferably from about 0.2 to 30 mg/kg, more preferably from about 0.5 mg to 15 mg. The daily parenteral dosage regimen about 0.1 to about 80 mg/kg of total body weight, preferably from about 0.2 to about 30 mg/kg, and more preferably from about 0.5 mg to 15 mg/kg. The daily topical dosage regimen will preferably be from 0.1 mg to 150 mg, administered one to four, preferably two or three times daily. The daily inhalation dosage regimen will preferably be from about 0.01 mg/kg to about 1 mg/kg per day. It will also be recognized by one of skill in the art that the optimal quantity and spacing of individual dosages of a compound of Formula (I) or a pharmaceutically acceptable salt thereof will be determined by the nature and extent of the condition being treated, the form, route and site of administration, and the particular patient being treated, and that such optimums can be determined by conventional techniques. It will also be appreciated by one of skill in the art that the optimal course of treatment, i.e., the number of doses of a compound of Formula (I) or a pharmaceutically acceptable salt thereof given per day for a defined number of days, can be ascertained by those skilled in the art using conventional course of treatment determination tests.

The invention will now be described by reference to the following biological examples which are merely illustrative and are not to be construed as a limitation of the scope of the present invention.

BIOLOGICAL EXAMPLES

The cytokine-inhibiting effects of compounds of the present invention were determined by the following in vitro assays:

Assays for Interleukin-1 (IL-1), Interleukin-8 (IL-8), and Tumour Necrosis Factor (TNF) are well known in the art, and may be found in a number of publications, and patents. Representative suitable assays for use herein are described in Adams et al., U.S. Pat. No. 5,593,992, whose disclosure is incorporated by reference in its entirety.

Interleukin-1 (IL-1)

Human peripheral blood monocytes are isolated and purified from either fresh blood preparations from volunteer donors, or from blood bank buffy coats, according to the procedure of Colotta et al, J Immunol, 132, 936 (1984). These monocytes ($1 \times 10^6$) are plated in 24-well plates at a concentration of 1–2 million/ml per well. The cells are allowed to adhere for 2 hours, after which time non-adherent cells are removed by gentle washing. Test compounds are then added to the cells for 1 h before the addition of lipopolysaccharide (50 ng/ml), and the cultures are incubated at 37° C. for an additional 24 h. At the end of this period, culture supernatants are removed and clarified of cells and all debris. Culture supernatants are then immediately assayed for IL-1 biological activity, either by the method of Simon et al., J. Immunol. Methods, 84, 85, (1985) (based on ability of IL-1 to stimulate a Interleukin 2 producing cell line (EL-4) to secrete IL-2, in concert with A23187 ionophore) or the method of Lee et al., J. ImmunoTherapy, 6 (1), 1–12 (1990) (ELISA assay).

In vivo TNF Assay (1) Griswold et al., *Drugs Under Exp. and Clinical Res.*, XIX (6), 243–248 (1993); or (2) Boehm, et al., *Journal Of Medicinal Chemistry* 39, 3929–3937 (1996) whose disclosures are incorporated by reference herein in their entirety.

LPS-induced TNFα Production in Mice and Rats

In order to evaluate in vivo inhibition of LPS-induced TNFα production in rodents, both mice and rats are injected with LPS.

Mouse Method

Male Balb/c mice from Charles River Laboratories are pretreated (30 minutes) with compound or vehicle. After the 30 min. pretreat time, the mice are given LPS (lipopolysaccharide from *Esherichia coli* Serotype 055-85, Sigma Chemical Co., St Louis, Mo.) 25 ug/mouse in 25 ul phosphate buffered saline (pH 7.0) intraperitoneally. Two hours later the mice are killed by $CO_2$ inhalation and blood samples are collected by exsanguination into heparinized blood collection tubes and stored on ice. The blood samples are centrifuged and the plasma collected and stored at −20° C. until assayed for TNFα by ELISA.

Rat Method

Male Lewis rats from Charles River Laboratories are pretreated at various times with compound or vehicle. After a determined pretreat time, the rats are given LPS (lipopolysaccharide from *Esherichia coli* Serotype 055-85, Sigma Chemical Co., St Louis, Mo.) 3.0 mg/kg intraperitoneally. The rats are killed by $CO_2$ inhalation and heparinized whole blood is collected from each rat by cardiac puncture 90 minutes after the LPS injection. The blood samples are centrifuged and the plasma collected for analysis by ELISA for TNFα levels.

ELISA Method

TNFα levels were measured using a sandwich ELISA, as described in Olivera et al., Circ. Shock, 37, 301–306, (1992), whose disclosure is incorporated by reference in its entirety herein, using a hamster monoclonal antimurine TNFα (Genzyme, Boston, Mass.) as the capture antibody and a polyclonal rabbit antimurine TNFa (Genzyme) as the second antibody. For detection, a peroxidase-conjugated goat anti-rabbit antibody (Pierce, Rockford, Ill.) was added, followed by a substrate for peroxidase (1 mg/ml orthophenylenediamine with 1% urea peroxide). TNFα levels in the plasma samples from each animal were calculated from a standard curve generated with recombinant murine TNFα (Genzyme).

LPS-Stimulated Cytokine Production in Human Whole Blood

Assay: Test compound concentrations were prepared at 10×concentrations and LPS prepared at 1 ug/ml (final conc. of 50 ng/ml LPS) and added in 50 uL volumes to 1.5 mL eppendorf tubes. Heparinized human whole blood was obtained from healthy volunteers and was dispensed into eppendorf tubes containing compounds and LPS in 0.4 mL volumes and the tubes incubated at 37 C. Following a 4 hour incubation, the tubes were centrifuged at 5000 rpm for 5 minutes in a TOMY microfuge, plasma was withdrawn and frozen at −80 C.

Cytokine measurement: IL-1 and/or TNF were quantified using a standardized ELISA technology. An in-house ELISA kit was used to detect human IL-1 and TNF. Concentrations of IL-1 or TNF were determined from standard curves of the appropriate cytokine and IC50 values for test compound (concentration that inhibited 50% of LPS-stimulated cytokine production) were calculated by linear regression analysis.

Prostoglandin Endoperoxide Synthase-2 (PGHS-2) Assay

This assay describes a method for determining the inhibitory effects of compounds of Formula (I) on human PGHS-2 protein expression in LPS stimulated human monocytes. A suitable assay for PGHS-2 protein expression may be found in a number of publications, including U.S. Pat. No. 5,593,992 whose disclosure is incorporated herein by reference.

CSBP Kinase Assay

This assay measures the CSBP-catalyzed transfer of $^{32}P$ from [a-$^{32}P$]ATP to threonine residue in an epidermal growth factor receptor (EGFR)-derived peptide (T669) with the following sequence: KRELVEPLTPSGEAPNQALLR (residues 661–68 1). (See Gallagher et al., "Regulation of Stress Induced Cytokine Production by Pyridinyl Imidazoles: Inhibition of CSPB Kinase", BioOrganic & Medicinal Chemistry, 1997, 5, 49–64).

Reactions were carried in round bottom 96 well plate (from Corning) in a 30 ml volume. Reactions contained (in final concentration): 25 mM Hepes, pH7.5; 10 mM $MgCl_2$; 0.17 mM ATP (the $Km_{[ATP]}$ of p38 (see Lee et al., Nature 300, n72 pg. 639–746 (December 1994) and Young et al., J. Biol. Chem. 272, n 18 pg. 12116–12121 (May 1997)); 2.5 uCi of [g-32P]ATP; 0.2 mM sodium orthovanadate; 1 mM DTT; 0.1% BSA; 10% glycerol; 0.67 mM T669 peptide; and 2–4 nM of yeast-expressed, activated and purified p38. Reactions were initiated by the addition of [gamma-32P] Mg/ATP, and incubated for 25 min at 37 C. Inhibitors (dissolved in DMSO) were incubated with the reaction mixture on ice for 30 minutes prior to adding the 32P-ATP. Final DMSO concentration was 0.16%. Reactions were terminated by adding 10 ul of 0.3 M phosphoric acid, and phosphorylated peptide was isolated from the reactions by capturing it on p81 phosphocellulose filters (Whatman). Filters were washed with 75 mM phosphoric acids, and incorporated 32P was quantified using beta scintillation counter. Under these conditions, the specific activity of p38 was 400–450 pmol/pmol enzyme, and the activity was linear for up to 2 hours of incubation. The kinase activity values were obtained after subtracting values generated in the absence of substrate which were 10–15% of total values.

Representative final compounds of Formula (I) and (II), Examples 2 and 4 have demonstrated positive inhibitory activity of an $IC_{50}$ of <50 uM in this binding assay. Example 3, upon retesting was not found active at this micromolar amount. Example 1 and Example 3 are expected to demonstrate positive inhibitory activity of an $IC_{50}$ of <100 uM in this binding assay.

TNF-α in Traumatic Brain Injury Assay

This assay provides for examination of the expression of tumor necrosis factor mRNA in specific brain regions which follow experimentally induced lateral fluid-percussion traumatic brain injury (TBI) in rats. Since TNF-a is able to induce nerve growth factor (NGF) and stimulate the release of other cytokines from activated astrocytes, this post-traumatic alteration in gene expression of TNF-a plays an important role in both the acute and regenerative response to CNS trauma. A suitable assay may be found in WO 97/35856 whose disclosure is incorporated herein by reference.

CNS Injury Model for IL-β mRNA

This assay characterizes the regional expression of interleukin-1β (IL-1β) mRNA in specific brain regions following experimental lateral fluid-percussion traumatic brain injury (TBI) in rats. Results from these assays indicate that following TBI, the temporal expression of IL-1β mRNA is regionally stimulated in specific brain regions. These regional changes in cytokines, such as IL-1β play a role in the post-traumatic pathologic or regenerative sequelae of brain injury. A suitable assay may be found in WO 97/35856 whose disclosure is incorporated herein by reference.

Angiogenesis Assay

Described in WO 97/32583, whose disclosure is incorporated herein by reference, is an assay for determination of inflammatory angiogenesis which may be used to show that cytokine inhibition will stop the tissue destruction of excessive or inappropriate proliferation of blood vessels.

All publications, including but not limited to patents and patent applications, cited in this specification are herein incorporated by reference as if each individual publication were specifically and individually indicated to be incorporated by reference herein as though fully set forth.

The above description fully discloses the invention including preferred embodiments thereof. Modifications and improvements of the embodiments specifically disclosed herein are within the scope of the following claims. Without further elaboration, it is believed that one skilled in the are can, using the preceding description, utilize the present invention to its fullest extent. Therefore the Examples herein are to be construed as merely illustrative and not a limitation of the scope of the present invention in any way. The embodiments of the invention in which an exclusive property or privilege is claimed are defined as follows:

What is claimed is:
1. A compound of the formula

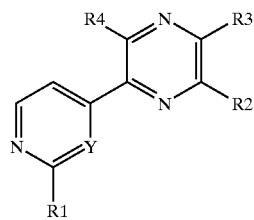

(I)

wherein
$R_1$ is hydrogen, X—$R_a$, optionally substituted $C_{1-4}$ alkyl, halogen, hydroxyl, optionally substituted $C_{1-4}$ alkoxy, optionally substituted $C_{1-4}$ alkylthio, optionally substituted $C_{1-4}$ alkylsulfinyl, $CH_2OR_{12}$, amino, mono and di- $C_{1-6}$ alkyl substituted amino, $N(R_{10})C(O)R_b$, $N(R_{10})S(O)_2R_d$, or an N-heterocyclyl ring which ring has from 5 to 7 members and optionally contains an additional heteroatom selected from oxygen, sulfur or $NR_{15}$;

Y is CH;

X is oxygen, sulfur or NH;

$R_a$ is $C_{1-6}$ alkyl, aryl, aryl$C_{1-6}$ alkyl, heterocyclic, heterocyclyl$C_{1-6}$ alkyl, heteroaryl, or heteroaryl$C_{1-6}$ alkyl moiety, wherein each of these moieties may be optionally substituted;

$R_b$ is hydrogen, $C_{1-6}$ alkyl, $C_{3-7}$ cycloalkyl, aryl, aryl$C_{1-4}$ alkyl, heteroaryl, heteroaryl$C_{1-4}$ alkyl, heterocyclyl, or heterocyclyl$C_{1-4}$ alkyl;

$R_d$ is $C_{1-6}$ alkyl, $C_{3-7}$ cycloalkyl, aryl, aryl$C_{1-4}$ alkyl, heteroaryl, heteroaryl$C_{1-4}$ alkyl, heterocyclyl, or heterocyclyl$C_{1-4}$ alkyl;

n is 0, or an integer having a value of 1 to 10;

v is 0, or an integer having a value of 1 or 2;

m is 0, or the integer having a value of 1 or 2;

m' is an integer having a value of 1 or 2;

m" is 0, or an integer having a value of 1 to 5;

$R_2$ and $R_3$ are independently hydrogen, $(CR_{10}R_{23})_nOR_9$, $(CR_{10}R_{23})_nOR_{11}$, $C_{1-10}$ alkyl, halo-substituted $C_{1-10}$ alkyl, $C_{2-10}$ alkenyl, $C_{2-10}$ alkynyl, $C_{3-7}$ cycloalkyl, $C_{3-7}$cycloalkyl$C_{1-10}$ alkyl, $C_{5-7}$ cycloalkenyl, $C_{5-7}$ cycloalkenyl $C_{1-10}$ alkyl, aryl, aryl$C_{1-10}$ alkyl, heteroaryl, heteroaryl$C_{1-10}$ alkyl, heterocyclyl, heterocyclyl$C_{1-10}$ alkyl, $(CR_{10}R_{23})_nS(O)_mR_{18}$, $(CR_{10}R_{23})_nNHS(O)_2R_{18}$, $(CR_{10}R_{23})_nNR_{13}R_{14}$, $(CR_{10}R_{23})_nNO_2$, $(CR_{10}R_{23})_nCN$, $(CR_{10}R_{23})_nS(O)_{m'}NR_{13}R_{14}$, $(CR_{10}R_{23})_nC(Z)R_{11}$, $(CR_{10}R_{23})_nOC(Z)R_{11}$, $(CR_{10}R_{23})_nC(Z)OR_{11}$, $(CR_{10}R_{23})_nC(Z)NR_{13}R_{14}$, $(CR_{10}R_{23})_nC(Z)NR_{11}OR_9$, $(CR_{10}R_{23})_nNR_{10}C(Z)R_{11}$, $(CR_{10}R_{23})_nNR_{10}C(Z)NR_{13}R_{14}$, $(CR_{10}R_{23})_nN(OR_6)C(Z)NR_{13}R_{14}$, $(CR_{10}R_{23})_nN(OR_6)C(Z)R_{11}$, $(CR_{10}R_{23})_nC(=NOR_6)R_{11}$, $(CR_{10}R_{23})_nNR_{10}C(=NR_{19})NR_{13}R_{14}$, $(CR_{10}R_{23})_nOC(Z)NR_{13}R_{14}$, $(CR_{10}R_{23})_nNR_{10}C(Z)NR_{13}R_{14}$, $(CR_{10}R_{23})_nNR_{10}C(Z)OR_{10}$, 5-($R_{18}$)-1,2,4-oxadizaol-3-yl or 4-($R_{12}$)-5-($R_{18}R_{19}$)-4,5-dihydro-1,2,4-oxadiazol-3-yl; wherein the cycloalkyl, cycloalkyl alkyl, aryl, arylalkyl, heteroaryl, heteroaryl alkyl, heterocyclic and heterocyclic alkyl moieties may be optionally substituted;

$R_4$ is phenyl, naphth-1-yl or naphth-2-yl ring, or a heteroaryl ring, which ring is optionally substituted independently by one to three substituents, and which, for a 4-phenyl, 4-naphth-1-yl, 5-naphth-2-yl or 6-naphth-2-yl substituent, is halogen, cyano, nitro, $C(Z,NR_7R_{17}$, $C(Z)OR_{16}$, $(CR_{10}R_{20})_vCOR_{12}$, $SR_5$, $S(O)R_5$, $OR_{12}$, halo-substituted-$C_{1-4}$ alkyl, $C_{1-4}$alkyl, $ZC(Z)R_{12}$, $NR_{10}C(Z)R_{16}$, or $(CR_{10}R_{20})_vNR_{10}R_{20}$ and which, for other positions of substitution, is halogen, cyano, nitro, phenyl, $C(Z)NR_{13}R_{14}$, $C(Z)OR_3$, $(CR_{10}R_{20})_{m"}COR_{25}$, $S(O)_mR_{25}$, $OR_{25}$, halosubstituted-$C_{1-4}$ alkyl, $C_{1-10}$ alkyl, $ZC(Z)R_{25}$, optionally substituted phenyl, $(CR_{10}R_{20})_{m"}NR_{10}C(Z)R_{25}$, $NR_{10}S(O)_mR_8$, $NR_{10}S(O)_mNR_7R_{17}$, or $(CR_{10}R_{20})_{m"}NR_{13}R_{14}$;

$R_5$ is hydrogen, $C_{1-4}$ alkyl, $C_{2-4}$ alkenyl, $C_{2-4}$ alkynyl or $NR_7R_{17}$, excluding the moieties $SR_5$ being $SNR_7R_{17}$ and $SOR_5$ being SOH;

$R_6$ is hydrogen, a pharmaceutically acceptable cation, $C_{1-10}$ alkyl, $C_{3-7}$ cycloalkyl, aryl, aryl$C_{1-4}$ alkyl, heteroaryl, heteroaryl$C_{1-4}$ alkyl, heterocyclic, aroyl, or $C_{1-10}$ alkanoyl;

$R_7$ and $R_{17}$ is each independently selected from hydrogen or $C_{1-4}$ alkyl or $R_7$ and $R_{17}$ together with the nitrogen to which they are attached form a heterocyclic ring of 5 to 7 members which ring optionally contains an additional heteroatom selected from oxygen, sulfur or $NR_{15}$;

$R_8$ is $C_{1-10}$ alkyl, halo-substituted $C_{1-10}$ alkyl, $C_{2-10}$ alkenyl, $C_{2-10}$ alkynyl, $C_{3-7}$ cycloalkyl, $C_{5-7}$ cycloalkenyl, aryl, aryl$C_{1-10}$ alkyl, heteroaryl, heteroaryl$C_{1-10}$ alkyl, $(CR_{10}R_{20})_nOR_{11}$, $(CR_{10}R_{20})_nS(O)_mR_{18}$, $(CR_{10}R_{20})_nNHS(O)_2R_{18}$, or $(CR_{10}R_{20})_nNR_{13}R_{14}$; wherein the aryl, arylalkyl, heteroaryl, heteroaryl alkyl moieties may be optionally substituted;

$R_9$ is hydrogen, $C(Z)R_{11}$ or optionally substituted $C_{1-10}$ alkyl, $S(O)_2R_{18}$, optionally substituted aryl or optionally substituted aryl$C_{1-4}$ alkyl;

$R_{10}$ and $R_{20}$ is each independently selected from hydrogen or $C_{1-4}$ alkyl;

$R_{11}$ is hydrogen, $C_{1-10}$ alkyl, $C_{3-7}$ cycloalkyl, heterocyclyl, heterocyclyl $C_{1-10}$ alkyl, aryl, aryl$C_{1-10}$ alkyl, heteroaryl or a heteroaryl$C_{1-10}$ alkyl moiety, wherein the aryl, arylalkyl, heteroaryl, heteroaryl alkyl, heterocyclyl or heterocyclylalkyl moieties may be optionally substituted;

$R_{12}$ is hydrogen or $R_{16}$;

$R_{13}$ and $R_{14}$ is each independently selected from hydrogen or optionally substituted $C_{1-4}$ alkyl, optionally substituted aryl or optionally substituted aryl-$C_{1-4}$alkyl, or together with the nitrogen which they are attached form a heterocyclic ring of 5 to 7 members which ring optionally contains an additional heteroatom selected from oxygen, sulfur or $NR_9$;

$R_{15}$ is hydrogen, $C_{1-4}$ alkyl or $C(Z)$—$C_{1-4}$ alkyl;

$R_{16}$ is $C_{1-4}$ alkyl, halo-substituted-$C_{1-4}$ alkyl, or $C_{3-7}$ cycloalkyl;

$R_{18}$ is $C_{1-10}$ alkyl, $C_{3-7}$ cycloalkyl, heterocyclyl, aryl, aryl$C_{1-10}$ alkyl, heterocyclyl, heterocyclyl-$C_{1-10}$ alkyl, heteroaryl or a heteroarylalkyl moiety, wherein the aryl, arylalkyl, heteroaryl, heteroaryl alkyl, heterocyclyl or heterocyclylalkyl moieties may be optionally substituted;

$R_{19}$ is hydrogen, cyano, $C_{1-4}$ alkyl, $C_{3-7}$ cycloalkyl or aryl;

$R_{23}$ is hydrogen, $C_{1-6}$ alkyl, $C_{3-7}$ cycloalkyl, aryl, aryl$C_{1-4}$ alkyl, heteroaryl, heteroaryl$C_{1-4}$ alkyl, heterocyclyl, or heterocyclyl$C_{1-4}$ alkyl moiety, all of which moieties may be optionally substituted;

R$_{25}$ is heterocyclyl, heterocyclylC$_{1-10}$ alkyl or R$_8$; and
Z is oxygen or sulfur;
or a pharmaceutically acceptable salt thereof.

2. The compound according to claim 1 wherein the optional substituent on the R$_1$ moiety is hydrogen, or Y, and Y is X$_1$—R$_a$, and X$_1$ is oxygen, sulfur or nitrogen.

3. The compound according to claim 2 wherein R$_4$ is an optionally substituted phenyl or napthyl.

4. The compound according to claim 3 wherein the phenyl or napthyl is substituted one or more times independently by halogen, SR$_5$, S(O)R$_5$, OR$_{12}$, halo-substituted-C$_{1-4}$ alkyl, or C$_{1-4}$ alkyl.

5. The compound according to claim 1 wherein R$_2$ is hydrogen.

6. The compound according to claim 1 which is
2-(4Fluorophenyl)-3-(pyridin-4-yl)pyrazine;
2-(6-Methoxy)napthyl-2-yl-3-(4-pyridyl)pyrazine,
2-Napthyl-2-yl-3-(4-pyridyl)pyrazine; or a pharmaceutically acceptable salt thereof.

7. A pharmaceutical composition comprising a compound according to claim 1 and a pharmaceutically acceptable carrier or diluent.

8. The compound according to claim 2 wherein Ra is an aryl, heterocyclic, heterocyclic alkyl, heteroaryl, heteroarylalkyl moiety optionally substituted one or more times independently with halogen; C$_{1-4}$ alkyl; halosubstituted alkyl; hydroxy; hydroxy substituted C$_{1-4}$ alkyl; C$_{1-4}$ alkoxy; S(O)$_m$alkyl and S(O)$_m$ aryl (wherein m is 0, 1, or 2); C(O)OR$_{11}$; C(Q)R$_{11}$; OC(O)R$_c$; O—(CH$_2$)s-O—, and s is 1 to 3; amino; mono- and di-C$_{1-6}$ alkyl substituted amino; N(R$_{10}$)C(O)R$_b$; N(R$_{10}$)S(O)$_2$R$_d$; C(O)NR$_{10}$R$_{20}$; S(O)$_2$(CR$_{10}$R$_{20}$)$_t$NR$_{13}$R$_{14}$ (wherein t is 0, or an integer of 1 to 3); cyano, nitro, or an N-heterocyclyl ring which ring has from 5 to 7 members and optionally contains an additional heteroatom selected from oxygen, sulfur or NR$_{15}$; aryl; an optionally substituted arylalkyl; aryloxy; or arylalkyloxy;

R$_c$ is hydrogen, optionally substituted C$_{1-6}$ alkyl, C$_{3-7}$ cycloalkyl, aryl, arylC$_{1-4}$ alkyl, heteroaryl, heteroarylC$_{1-4}$alkyl, heterocyclyl, or heterocyclylC$_{1-4}$ alkyl moiety, wherein all of which may be optionally substituted.

9. The compound according to claim 1 wherein R$_1$ is hydrogen.

10. The compound according to claim 5 wherein R$_3$ is hydrogen.

11. The compound according to claim 6 wherein R$_1$ is hydrogen.

12. A compound of the formula:

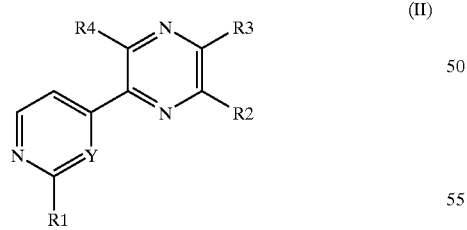

(II)

wherein
R$_1$ is hydrogen, X—R$_a$, optionally substituted C$_{1-4}$ alkyl, halogen, hydroxyl, optionally substituted C$_{1-4}$ alkoxy, optionally substituted C$_{1-4}$ alkylthio, optionally substituted C$_{1-4}$ alkylsulfinyl, CH$_2$OR$_{12}$, amino, mono and di- C$_{1-6}$ alkyl substituted amino, N(R$_{10}$)C(O)R$_b$, N(R$_{10}$)S(O)$_2$R$_d$, or an N-heterocyclyl ring which ring has from 5 to 7 members and optionally contains an additional heteroatom selected from oxygen, sulfur or NR$_{15}$;

Y is CH;
X is oxygen, sulfur or NH;
R$_a$ is C$_{1-6}$ alkyl, aryl, arylC$_{1-6}$ alkyl, heterocyclic, heterocyclyC$_{1-6}$ alkyl, heteroaryl, or heteroarylC$_{1-6}$ alkyl moiety, wherein each of these moieties may be optionally substituted;
R$_b$ is hydrogen, C$_{1-6}$ alkyl, C$_{3-7}$ cycloalkyl, aryl, arylC$_{1-4}$ alkyl, heteroaryl, heteroarylC$_{1-4}$ alkyl, heterocyclyl, or heterocyclylC$_{1-4}$ alkyl;
R$_d$ is C$_{1-6}$ alkyl, C$_{3-7}$ cycloalkyl, aryl, arylC$_{1-4}$ alkyl, heteroaryl, heteroarylC$_{1-4}$ alky heterocyclyl, or heterocyclylC$_{1-4}$ alkyl;
n is 0, or an integer having a value of 1 to 10;
v is 0, or an integer having a value of 1 or 2;
m is 0, or the integer having a value of 1 or 2;
m' is an integer having a value of 1 or 2;
m" is 0. or an integer having a value of 1 to 5;
R$_2$ and R$_3$ are independently hydrogen, (CR$_{10}$R$_{23}$)$_n$OR$_9$, (CR$_{10}$R$_{23}$)$_n$OR$_{11}$, C$_{1-10}$ alkyl, halo-substituted C$_{1-10}$ alkyl, C$_{2-10}$ alkenyl, C$_{2-10}$ alkynyl, C$_{3-7}$ cycloalkyl, C$_{3-7}$cycloalkylC$_{1-10}$ alkyl, C$_{5-7}$ cycloalkenyl, C$_{5-7}$ cycloalkenyl C$_{1-10}$ alkyl, aryl, arylC$_{1-10}$ alkyl, heteroaryl, heteroarylC$_{1-10}$ alkyl, heterocyclyl, heterocyclylC$_{1-10}$ alkyl, (CR$_{10}$OR$_{23}$)$_n$S(O)$_m$R$_{18}$, (CR$_{10}$R$_{23}$)$_n$NHS(O)$_2$R$_{18}$,(CR$_{10}$R$_{23}$)$_n$NR$_{13}$R$_{14}$, (CR$_{10}$R$_{23}$)$_n$NO$_2$, (CR$_{10}$R$_{23}$)$_n$CN, (CR$_{10}$R$_{23}$)$_n$S(O)$_m$NR$_{13}$R$_{14}$, (CR$_{10}$R$_{23}$)$_n$C(Z)R$_{11}$, (CR$_{10}$R$_{23}$)$_n$OC(Z)R$_{11}$, (CR$_{10}$R$_{23}$)$_n$C(Z)OR$_{11}$, (CR$_{10}$R$_{23}$)$_n$C(Z)NR$_{13}$R$_{14}$, (CR$_{10}$R$_{23}$)$_n$C(Z)NR$_{11}$OR$_9$, (CR$_{10}$R$_{23}$)$_n$NR$_{10}$C(Z)R$_{11}$, (CR$_{10}$R$_{23}$)$_n$NR$_{10}$C(Z)NR$_{13}$R$_{14}$, (CR$_{10}$R$_{23}$)$_n$N(OR$_6$)C(Z)NR$_{13}$R$_{14}$, (CR$_{10}$R$_{23}$)$_n$N(OR$_6$)C(Z)R$_{11}$, (CR$_{10}$R$_{23}$)$_n$C(=NOR$_6$)R$_{11}$, (CR$_{10}$R$_{23}$)$_n$NR$_{10}$C(=NR$_{19}$)NR$_{13}$R$_{14}$, (CR$_{10}$R$_{23}$)$_n$OC(Z)NR$_{13}$R$_{14}$, (CR$_{10}$R$_{23}$)$_n$NR$_{10}$C(Z)NR$_{13}$R$_{14}$, (CR$_{10}$R$_{23}$)$_n$NR$_{10}$C(Z)OR$_{10}$, 5-(R$_{18}$)-1,2,4-oxadizaol-3-yl or 4-(R$_{12}$)-5-(R$_{18}$R$_{19}$)-4,5-dihydro-1,2,4-oxadiazol-3-yl; wherein the cycloalkyl, cycloalkyl alkyl, aryl, arylalkyl, heteroaryl, heteroaryl alkyl, heterocyclic and heterocyclic alkyl moieties may be optionally substituted;

R$_4$ is phenyl, naphth-1-yl or naphth-2-yl ring, or a heteroaryl ring, which ring is optionally substituted independently by one to three substituents, and which, for a 4-phenyl, 4-naphth-1-yl, 5-naphth-2-yl or 6-naphth-2-yl substituent, is halogen, cyano, nitro, C(Z)NR$_7$R$_{17}$, C(Z)OR$_{16}$, (CR$_{10}$R$_{20}$)$_v$COR$_{12}$, SR$_5$, S(O)R$_5$, OR$_{12}$, halo-substituted-C$_{1-4}$ alkyl, C$_{1-4}$alkyl, ZC(Z)R$_{12}$, NR$_{10}$C(Z)R$_{16}$, or (CR$_{10}$R$_{20}$)vNR$_{10}$R$_{20}$ and which, for other positions of substitution, is halogen, cyano, nitro, phenyl, C(Z)NR$_{13}$R$_{14}$, C(Z)OR$_{25}$, (CR$_{10}$R$_{20}$)$_{m"}$COR$_{25}$, S(O)$_m$R$_{25}$, OR$_{25}$, halosubstituted-C$_{1-4}$ alkyl, C$_{1-10}$ alkyl, ZC(Z)R$_{25}$, optionally substituted phenyl, (CR$_{10}$R$_{20}$)$_{m"}$NR$_{10}$C(Z)R$_{25}$, NR$_{10}$S(O)$_m$R$_8$, NR$_{10}$S(O)$_{m'}$NR$_7$R$_{17}$, or (CR$_{10}$R$_{20}$)$_{m"}$NR$_{13}$R$_{14}$;
R$_5$ is hydrogen, C$_{1-4}$ alkyl, C$_{2-4}$ alkenyl, C$_{2-4}$ alkynyl or NR$_7$R$_{17}$, excluding the moieties SR$_5$ being SNR$_7$R$_{17}$ and SOR$_5$ being SOH;
R$_6$ is hydrogen, a pharmaceutically acceptable cation, C$_{1-10}$ alkyl, C$_{3-7}$ cycloalkyl, aryl, arylC$_{1-4}$ alkyl, heteroaryl, heteroarylC$_{1-4}$ alkyl, heterocyclic, aroyl, or C$_{1-10}$ alkanoyl;
R$_7$ and R$_{17}$ is each independently selected from hydrogen or C$_{1-4}$ alkyl or R$_7$ and R$_{17}$ together with the nitrogen to which they are attached form a heterocyclic ring of 5 to 7 members which ring optionally contains an additional heteroatom selected from oxygen, sulfur or NR$_{15}$;

$R_8$ is $C_{1-10}$ alkyl, halo-substituted $C_{1-10}$ alkyl, $C_{2-10}$ alkenyl, $C_{2-10}$ alkynyl, $C_{3-7}$ cycloalkyl, $C_{5-7}$ cycloalkenyl, aryl, aryl$C_{1-10}$ alkyl, heteroaryl, heteroaryl$C_{1-10}$ alkyl, $(CR_{10}R_{20})_nOR_{11}$, $(CR_{10}R_{20})_nS(O)_mR_{18}$, $(CR_{10}R_{20})_nNHS(O)_2R_{18}$, or $(CR_{10}R_{20})_nNR_{13}R_{14}$; wherein the aryl, arylalkyl, heteroaryl, heteroaryl alkyl moieties may be optionally substituted;

$R_9$ is hydrogen, $C(Z)R_{11}$ or optionally substituted $C_{1-10}$ alkyl, $S(O)_2R_{18}$, optionally substituted aryl or optionally substituted aryl$C_{1-4}$ alkyl;

$R_{10}$ and $R_{20}$ is each independently selected from hydrogen or $C_{1-4}$ alkyl;

$R_{11}$ is hydrogen, $C_{1-10}$ alkyl, $C_{3-7}$ cycloalkyl, heterocyclyl, heterocyclyl $C_{1-10}$alkyl, aryl, aryl$C_{1-10}$ alkyl, heteroaryl or a heteroaryl$C_{1-10}$ alkyl moiety, wherein the aryl, arylalkyl, heteroaryl, heteroaryl alkyl, heterocyclyl or heterocyclylalkyl moieties may be optionally substituted;

$R_{12}$ is hydrogen or $R_{16}$;

$R_{13}$ and $R_{14}$ is each independently selected from hydrogen or optionally substituted $C_{1-4}$ alkyl, optionally substituted aryl or optionally substituted aryl-$C_{1-4}$alkyl, or together with the nitrogen which they are attached form a heterocyclic ring of 5 to 7 members which ring optionally contains an additional heteroatom selected from oxygen, sulfur or $NR_9$;

$R_{15}$ is hydrogen, $C_{1-4}$ alkyl or $C(Z)$—$C_{1-4}$ alkyl;

$R_{16}$ is $C_{1-4}$ alkyl, halo-substituted-$C_{1-4}$ alkyl, or $C_{3-7}$ cycloalkyl;

$R_{18}$ is $C_{1-10}$ alkyl, $C_{3-7}$ cycloalkyl, heterocyclyl, aryl, aryl$C_{1-10}$ alkyl, heterocyclyl, heterocyclyl-$C_{1-10}$ alkyl, heteroaryl or a heteroarylalkyl moiety, wherein the aryl, arylalkyl, heteroaryl, heteroaryl alkyl, heterocyclyl or heterocyclylalkyl moieties may be optionally substituted;

$R_{19}$ is hydrogen, cyano, $C_{1-4}$ alkyl, $C_{3-7}$ cycloalkyl or aryl;

$R_{23}$ is hydrogen, $C_{1-6}$ alkyl, $C_{3-7}$ cycloalkyl, aryl, aryl$C_{1-4}$ alkyl, heteroaryl, heteroaryl$C_{1-4}$ alkyl, heterocyclyl, or heterocyclyl$C_{1-4}$ alkyl moiety, all of which moieties may be optionally substituted;

$R_{25}$ is heterocyclyl, heterocyclyl$C_{1-10}$ alkyl or $R_8$; and

Z is oxygen or sulfur;

or a pharmaceutically acceptable salt thereof.

13. The compound according to claim 12 wherein $R_1$ is an optionally substituted pyrid-4-yl.

14. The compound according to claim 13 wherein the optional substituent is Y.

15. The compound according to claim 13 wherein $R_4$ is an optionally substituted phenyl or napthyl.

16. The compound according to claim 15 wherein the phenyl or napthyl is substituted one or more times independently by halogen, $SR_5$, $S(O)R_5$, $OR_{12}$, halo-substituted-$C_{1-4}$ alkyl, or $C_{1-4}$ alkyl.

17. The compound according to claim 12 wherein $R_2$ is hydrogen.

18. The compound according to claim 12 which is 2,3-Dihydro-5-(4-Fluorophenyl)-3-(pyridin-4-yl)pyrazine, or a pharmaceutically acceptable salt thereof.

19. A pharmaceutical composition comprising a compound according to claim 12 and a pharmaceutically acceptable carrier or diluent.

20. A method of treating a CSBP/RK/p38 kinase mediated disease, in a mammal in need thereof, which comprises administering to said mammal an effective amount of a compound of Formula (II) according to claim 12.

21. The method according to claim 20 wherein the CSBP/RK/p38 kinase mediated disease is psoriatic arthritis, Reiter's syndrome, gout, traumatic arthritis, rubella arthritis and acute synovitis, rheumatoid arthritis, rheumatoid spondylitis, osteoarthritis, gouty arthritis and other arthritic condition, sepsis, septic shock, endotoxic shock, gram negative sepsis, toxic shock syndrome, cerebral malaria, meningitis, ischemic and hemorrhagic stroke, neurotrauma/closed head injury, asthma, adult respiratory distress syndrome, chronic pulmonary inflammatory disease, chronic obstructive pulmonary disease, silicosis, pulmonary sarcososis, bone resorption disease, osteoporosis, restenosis, cardiac, brain and renal reperfusion injury, thrombosis, glomerularnephritis, chronic renal failure, diabetes, diabetic retinopathy, macular degeneration, graft vs. host reaction, allograft rejection, inflammatory bowel disease, Crohn's disease, ulcerative colitis, neurodegenrative disease, muscle degeneration, diabetic retinopathy, macular degeneration, tumor growth and metastasis, angiogenic disease, rhinovirus infection, eczema, contact dermatitis, psoriasis, sunburn, and conjunctivitis.

22. A method of treating a CSBP/RK/p38 kinase mediated disease, in a mammal in need thereof, which comprises administering to said mammal an effective amount of a compound of Formula (I) according to claim 1.

23. The method according to claim 22 wherein the CSBP/RK/p38 kinase mediated disease is psoriatic arthritis, Reiter's syndrome, gout, traumatic arthritis, rubella arthritis and acute synovitis, rheumatoid arthritis, rheumatoid spondylitis, osteoarthritis, gouty arthritis and other arthritic condition, sepsis, septic shock, endotoxic shock, gram negative sepsis, toxic shock syndrome, cerebral malaria, meningitis, ischemic and hemorrhagic stroke, neurotrauma/closed head injury, asthma, adult respiratory distress syndrome, chronic pulmonary inflammatory disease, chronic obstructive pulmonary disease, silicosis, pulmonary sarcososis, bone resorption disease, osteoporosis, restenosis, cardiac, brain and renal reperfusion injury, thrombosis, glomerulamephritis, chronic renal failure, diabetes, diabetic retinopathy, macular degeneration, graft vs. host reaction, allograft rejection, inflammatory bowel disease Crohn's disease, ulcerative colitis, neurodegenrative disease, muscle degeneration, diabetic retinopathy, macular degeneration, tumor growth and metastasis, angiogenic disease, rhinovirus infection, eczema, contact dermatitis, psoriasis, sunburn, and conjunctivitis.

* * * * *